(12) United States Patent
Kitaoka

(10) Patent No.: US 9,993,010 B2
(45) Date of Patent: Jun. 12, 2018

(54) CAROTENOID-CONTAINING COMPOSITION AND METHOD FOR PRODUCING SAME

(71) Applicant: FUJIFILM CORPORATION, Tokyo (JP)

(72) Inventor: Hiroyuki Kitaoka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 784 days.

(21) Appl. No.: 14/278,997

(22) Filed: May 15, 2014

(65) Prior Publication Data

US 2014/0248410 A1 Sep. 4, 2014

Related U.S. Application Data

(63) Continuation of application No. PCT/JP2012/079670, filed on Nov. 15, 2012.

(30) Foreign Application Priority Data

Nov. 18, 2011 (JP) .................................. 2011-253084

(51) Int. Cl.
| | |
|---|---|
| A23D 7/005 | (2006.01) |
| A61Q 19/00 | (2006.01) |
| A61K 8/37 | (2006.01) |
| A61K 8/31 | (2006.01) |
| A61K 47/14 | (2017.01) |
| A61K 47/06 | (2006.01) |
| A61K 31/07 | (2006.01) |
| A61K 8/39 | (2006.01) |
| A61K 31/01 | (2006.01) |
| A23D 7/01 | (2006.01) |
| A23L 33/105 | (2016.01) |
| A23L 33/15 | (2016.01) |
| A23L 33/155 | (2016.01) |

(52) U.S. Cl.
CPC ............ *A23D 7/0053* (2013.01); *A23D 7/011* (2013.01); *A23L 33/105* (2016.08); *A23L 33/15* (2016.08); *A23L 33/155* (2016.08); *A61K 8/31* (2013.01); *A61K 8/37* (2013.01); *A61K 8/375* (2013.01); *A61K 8/39* (2013.01); *A61K 31/01* (2013.01); *A61K 31/07* (2013.01); *A61K 47/06* (2013.01); *A61K 47/14* (2013.01); *A61Q 19/00* (2013.01); *A61K 2800/10* (2013.01); *A61K 2800/21* (2013.01); *A61K 2800/522* (2013.01)

(58) Field of Classification Search
CPC ..... A23D 7/0053; A23D 7/011; A23L 33/155; A23L 33/15; A23L 33/105; A61K 8/37; A61K 31/01; A61K 47/06; A61K 8/39; A61K 8/31; A61K 8/375; A61K 47/14; A61K 31/07; A61K 2800/522; A61Q 19/00

See application file for complete search history.

(56) References Cited

U.S. PATENT DOCUMENTS

| | | |
|---|---|---|
| 5,364,563 A | 11/1994 | Cathrein et al. |
| 2002/0110599 A1 | 8/2002 | Auweter et al. |
| 2007/0286930 A1 | 12/2007 | Ogawa et al. |
| 2010/0316581 A1 | 12/2010 | Takeoka et al. |
| 2011/0275592 A1 | 11/2011 | Tanisaka |
| 2012/0039970 A1 | 2/2012 | Kopsel et al. |
| 2013/0071451 A1 | 3/2013 | Serizawa |
| 2013/0172426 A1 | 7/2013 | Oda et al. |
| 2013/0337136 A1 | 12/2013 | Serizawa |

FOREIGN PATENT DOCUMENTS

| | | |
|---|---|---|
| CN | 103391725 A | 11/2013 |
| JP | 3-66615 | 3/1991 |
| JP | 6-172170 A | 6/1994 |
| JP | 9-157159 A | 6/1997 |
| JP | 10-120933 A | 5/1998 |
| JP | 2006-129841 A | 5/2006 |
| JP | 2008-143841 A | 6/2006 |
| JP | 2007-289749 A | 10/2007 |
| JP | 2008-013751 A | 1/2008 |
| JP | 2009-155326 | 7/2009 |
| JP | 2009-189335 A | 8/2009 |
| KR | 10-2011-0112431 A | 10/2011 |
| WO | 2009-093595 A1 | 7/2009 |
| WO | 2010/084789 A1 | 7/2010 |
| WO | WO 2010/112406 A1 | 10/2010 |
| WO | 2011/145659 A1 | 11/2011 |
| WO | WO 2012/11157 A1 | 8/2012 |

OTHER PUBLICATIONS

Extended European Search Report issued in European Patent Application No. 12849558.7 dated May 29, 2015.
Korean Office Action dated Jan. 7, 2016, for Korean Application No. 10-2014-7013232 with the partial English translation.
Japan Office Action issued in Japan Patent Application No. 2012-251433 dated Mar. 24, 2015.
Third Party Submission in Japanese Application No. 2012-251433 on Apr. 14, 2015.
Chinese Office Action issued in Chinese Patent Application No. 201260056186.1 dated Mar. 17, 2015.
International Search Report issued in PCT/JP2012/079670, dated Dec. 18, 2012.

(Continued)

*Primary Examiner* — Nikki H. Dees
(74) *Attorney, Agent, or Firm* — Birch, Stewart, Kolasch & Birch, LLP

(57) ABSTRACT

A carotenoid-containing composition including: a carotenoid component containing a crystalline carotenoid that is in an amorphous state; a (poly)glycerol fatty acid ester that contains from one to six glycerol units and from one to six fatty acid units and has at least one hydroxyl group resulting from a glycerol unit; a fatty acid ester component which is at least one selected from the group consisting of triesters of glycerol and fatty acids, and esters of alcohols having one hydroxyl group and fatty acids, contains no hydroxyl group in a molecule, and has from 10 to 60 carbon atoms in total; and an antioxidant.

9 Claims, No Drawings

(56) References Cited

OTHER PUBLICATIONS

Written Opinion issued in PCT/JP2012/079670, dated Dec. 18, 2012.
Chinese Office Action issued in Chinese Patent Application No. 2012800561861 dated Sep. 15, 2015 (with Partial English translation).
Sekine et al. "Colloid Chemistry: Developments and Current Situation", Jun. 5, 1987, pp. 100-101.
Sekine et al., "New cosmetics Handbook", Oct. 30, 2006, pp. 415-418.
Third Party Submission in Japanese Application No. 2012-251433 on Jan. 6, 2015.
Korean Office Action for Korean Application No. 10-2014-7013232, dated Jul. 1, 2016, with a partial English translation.
European Office Action, dated Mar. 21, 2017, for European Application No. 12 849 558.7.

CAROTENOID-CONTAINING COMPOSITION AND METHOD FOR PRODUCING SAME

CROSS-REFERENCE TO RELATED APPLICATIONS

This application is a continuation application of International Application No. PCT/JP2012/079670, filed Nov. 15, 2012, which is incorporated herein by reference. Further, this application claims priority from Japanese Patent Application No. 2011-253084, filed Nov. 18, 2011, which is incorporated herein by reference.

TECHNICAL FIELD

The present invention relates to a carotenoid-containing composition and a method of producing the carotenoid-containing composition.

BACKGROUND ART

In recent years, various compositions containing carotenoids have been proposed with focusing on the high functionalities of the carotenoids. Since a carotenoid is generally widely known as an insoluble ingredient, it is usually adopted in a form of an emulsion composition.

Specific examples of known emulsion compositions containing carotenoids include: a carotenoid-containing emulsion composition, an aqueous phase of which containing at least one water-soluble emulsifier, and an oil phase of which containing tocopherol and lecithin (e.g., see Japanese Patent Application Laid-Open (JP-A) No. 2008-13751); a carotenoid dye solubilized liquid preparation for a food product in which a composition of a carotenoid dye for a food product and a polyglycerol fatty acid ester is microparticulated, and which has a transmittance of 99% or more at 660 nm in a case of having an absorbance of 1 at a maximum absorption wavelength (e.g., see Japanese Patent Application Laid-Open (JP-A) No. H10-120933) in a visible range; and a carotenoid-containing composition obtained by emulsifying an oil phase, obtained by dissolving a carotenoid in an oil or a fat, in an aqueous phase containing a polyhydric alcohol in the presence of a polyglycerol fatty acid ester and lecithin, in which the oil phase has an average particle diameter of 100 nm or less (e.g., see Japanese Patent Application Laid-Open (JP-A) No. H09-157159).

SUMMARY OF INVENTION

Technical Problem

However, a crystalline carotenoid such as lycopene has high crystallinity, and in the case of preparing, for example, an emulsion composition, it often remains in a form of a crystal. There are cases in which in a composition containing a crystal as described above cannot exhibit an expected effect due to the presence of the crystal.

A first aspect of the invention may provide a carotenoid-containing composition which can stably contain a crystalline carotenoid in an amorphous state.

A second aspect of the invention may provide a method of producing a carotenoid-containing composition in which crystallization is suppressed even in a case in which the composition contains a carotenoid having high crystallinity.

Solution to Problem

The invention is as follows.

[1] A carotenoid-containing composition comprising:
a carotenoid component comprising a crystalline carotenoid that is in an amorphous state;
a (poly)glycerol fatty acid ester that comprises from one to six glycerol units, from one to six fatty acid units, and at least one hydroxyl group derived from a glycerol unit;
a fatty acid ester component which is at least one selected from the group consisting of a triester of glycerol and fatty acids and an ester of an alcohol having one hydroxyl group and a fatty acid, comprises no hydroxyl group in a molecule, and has from 10 to 60 carbon atoms in total; and
an antioxidant.

[2] The carotenoid-containing composition according to [1], wherein a content of the crystalline carotenoid that is in an amorphous state is 50 mass % or more with respect to a total content of the carotenoid component.

[3] The carotenoid-containing composition according to [1] or [2], wherein a content of the fatty acid ester component is from 3 times to 300 times a total content of the carotenoid component, based on mass.

[4] The carotenoid-containing composition according to any of from [1] to [3], wherein a total content of the (poly)glycerol fatty acid ester is from 0.01 times to 9 times a total content of the crystalline carotenoid, based on mass.

[5] The carotenoid-containing composition according to any of from [1] to [4], wherein a content of the fatty acid ester component is from 0.8 times to 750 times a total content of the (poly)glycerol fatty acid ester, based on mass.

[6] The carotenoid-containing composition according to any of from [1] to [5], wherein the crystalline carotenoid is lycopene.

[7] The carotenoid-containing composition according to any of from [1] to [6], wherein the antioxidant comprises at least one selected from the group consisting of a compound having a phenolic hydroxyl group and an ascorbic acid compound.

[8] The carotenoid-containing composition according to any of from [1] to [7], wherein the antioxidant comprises at least one selected from the group consisting of aromatic carboxylic acids, cinnamic acids and ellagic acids.

[9] The carotenoid-containing composition according to any of from [1] to [8], wherein 90 mass % or more of the crystalline carotenoid is in an amorphous state.

[10] The carotenoid-containing composition according to any of from [1] to [9], wherein the carotenoid-containing composition is an oil-in-water emulsion composition comprising dispersed particles having an average particle diameter in a range of from 30 nm to 100 nm and comprising the carotenoid component.

[11] A method of producing a carotenoid-containing composition comprising heating, under a temperature condition of 90° C. or more, an oil phase component-mixture liquid, the oil phase component mixture liquid comprising:
a carotenoid component comprising at least one crystalline carotenoid;
a (poly)glycerol fatty acid ester that comprises from one to six glycerol units, from one to six fatty acid units, and at least one hydroxyl group derived from a glycerol unit;
a fatty acid ester component that is at least one selected from the group consisting of a triester of glycerol and fatty acids and an ester of an alcohol having one hydroxyl group and a fatty acid, comprises no hydroxyl group in a molecule, and has from 10 to 60 carbon atoms in total; and
an antioxidant.

Advantageous Effects of Invention

According to the first aspect of the invention, a carotenoid-containing composition that can stably contain a crystalline carotenoid in an amorphous state can be provided.

According to the second aspect of the invention, a method of producing a carotenoid-containing composition in which crystallization is suppressed even in a case in which the composition contains a carotenoid having high crystallinity can be provided.

DESCRIPTION OF EMBODIMENTS

The carotenoid-containing composition according to one embodiment of the invention includes: a carotenoid component containing a crystalline carotenoid that is in an amorphous state; a (poly)glycerol fatty acid ester that contains from one to six glycerol units, from one to six fatty acid units, and at least one hydroxyl group derived from a glycerol unit; a fatty acid ester component which is at least one selected from the group consisting of a triester of glycerol and fatty acids and an ester of an alcohol having one hydroxyl group and a fatty acid, contains no hydroxyl group in a molecule, and has from 10 to 60 carbon atoms in total; and an antioxidant.

Since the carotenoid-containing composition contains the defined (poly)glycerol fatty acid ester, the defined fatty acid ester component, and an antioxidant, as well as a carotenoid component containing a crystalline carotenoid, the crystalline carotenoid can be maintained in an amorphous state. Further, decomposition or disappearance of the carotenoid during and after the preparation of the carotenoid-containing composition can be effectively suppressed. As a result, the crystalline carotenoid in an amorphous state can be stably maintained in the composition.

In this specification, a numerical range indicates a range that includes a numerical value expressed as a lower limit value of the numerical range as the minimum value and a numerical value expressed as an upper limit value of the numerical range as the maximum value.

In the case of referring to an amount of a certain component in a composition, in a case in which plural substances corresponding to the component are present in the composition, the amount of the component means a total amount of the plural substances which are present in the composition, unless otherwise specified.

The term "step" includes not only an independent process, but also one that cannot be clearly distinguished from other process, as long as the predetermined action of this step is achieved thereby.

The expression "(poly)glycerol fatty acid ester" encompasses all of a glycerol fatty acid ester including one glycerol unit and one fatty acid unit, a glycerol fatty acid ester including plural units of either one thereof, and a glycerol fatty acid ester including plural units of both thereof.

The expression that one compound which is contained in a fatty acid ester component "contains no hydroxyl group in the molecule" means that the compound contained in the fatty acid ester component does not have any hydroxyl group in the molecule or as a substituent.

<Carotenoid-Containing Composition>

The carotenoid-containing composition according to one embodiment of the invention may be in any form as long as the carotenoid-containing composition contains a carotenoid component containing a crystalline carotenoid that is in an amorphous state; a (poly)glycerol fatty acid ester that contains from one to six glycerol units and from one to six fatty acid units and has at least one hydroxyl group derived from a glycerol unit; a fatty acid ester component which is at least one selected from the group consisting of triesters of glycerol and fatty acids, and esters of alcohols having one hydroxyl group and fatty acids, contains no hydroxyl group in the molecule, and has from 10 to 60 carbon atoms in total; and an antioxidant. The carotenoid-containing composition may be an oil phase composition composed only of a component included in an oil phase (hereinafter also simply referred to as an "oil phase component"), or an oil-in-water emulsion composition obtained by emulsification-mixing of the oil phase composition with an aqueous phase composition containing a certain water-soluble component.

[Carotenoid Component]

The carotenoid component in the carotenoid-containing composition contains a crystalline carotenoid that is in an amorphous state.

Since the crystalline carotenoid contained in the carotenoid component is in an amorphous state, the absorptivity of the carotenoid component into a body can be enhanced.

It may be confirmed using known means for detecting a crystal structure that a crystalline carotenoid is in an amorphous state. A carotenoid may be confirmed as a crystalline carotenoid by a usual method, for which, for example, differential scanning calorimetry (DSC), observation by a polarizing microscope, and X-ray diffraction can be used. An absence of detection of any crystal by these known technologies can define a subject as being amorphous. In particular, it is preferable to confirm amorphousness based on a presence of a DSC endothermic peak. Specifically, endothermic and exothermic temperatures are determined for a subject, which is freeze-dried to remove water therefrom when it is an emulsion or which is as it is when it is an oily composition or a powdery composition, in one cycle of from temperature-rise to temperature-fall (15° C./min) in a temperature range of from 30° C. to 200° C. using a DSC Q2000 (trade name, manufactured by TA Instruments Japan Inc.), and the absence of any recognizable endothermic peak is defined as an amorphous state.

The crystal ratio of the crystalline carotenoid in the carotenoid-containing composition is preferably from 0% to 50%, more preferably from 0% to 10%, and still more preferably from 0% to 5%, in view of dynamic absorptivity. As used herein, the term "crystal ratio" refers to a content (mass) of the crystalline carotenoid that is crystalline with respect to a total content (mass) of the carotenoid component contained in the carotenoid-containing composition. In other words, it is preferable that from at least 50 mass % to 100 mass % of the crystalline carotenoid is in an amorphous state, it is more preferable that from 90 mass % to 100 mass % of the crystalline carotenoid is in an amorphous state, and it is still more preferable that from 95 mass % to 100 mass % of the crystalline carotenoid is in an amorphous state.

An expected effect can be sufficiently obtained in a case in which 50 mass % or more of the crystalline carotenoid is in an amorphous state. Further, fine dispersed particles can be obtained, for example, in a case of preparing an emulsion composition.

For example, a comparison of the endothermic quantity of an endothermic peak from a carotenoid crystal in the composition measured by differential scanning calorimetry (DSC) with the endothermic quantity of the endothermic peak of a carotenoid crystal sample enables confirmation that the carotenoid component contains at least 50 mass % of the crystalline carotenoid that is in an amorphous state.

A comparison of the spectra of the composition in X-ray diffraction with the spectra of a carotenoid crystal sample also enables the confirmation.

A content of the crystalline carotenoid that is in an amorphous state can be converted and determined from a DSC peak area or a result obtained by XRD (X-ray diffraction) on basis that a value obtained for a carotenoid reagent which is a commercially available crystal as being 100%. Examples of the commercially available of the carotenoid reagent which is a crystal include biochemical reagents available from Wako Pure Chemical Industries, Ltd.

As used herein, "crystalline carotenoid" does not mean a specific carotenoid but means a carotenoid which can be present as a crystal substance at any temperature in a temperature range of from −5° C. to 35° C., in a case of being in a form of an oil, a paste, or the like containing the carotenoid, depending on various factors such as a production method, treatment, and storage thereof. In particular, lycopene, β-carotene, δ-carotene, zeaxanthin, lutein, astaxanthin, and the like described below are carotenoids that are easily present in a form of a crystal.

Examples of the crystalline carotenoid include dyes that are from terpenoids with from yellow to red and are derived from plants, algae, or bacteria. The crystalline carotenoid is not limited to those derived from natural origins but may be any crystalline carotenoid as long as it is obtained according to usual methods. A crystalline carotenoid may be confirmed by a usual method, for which, for example, differential scanning calorimetry (DSC), observation by a polarizing microscope, X-ray diffraction, and the like can be applied.

Specific examples of the crystalline carotenoid include lycopene, α-carotene, β-carotene, γ-carotene, δ-carotene, actinioerythrol, bixin, canthaxanthin, capsorubin, β-8'-apo-carotenal (apocarotenal), β-12'-apo-carotenal, xanthophylls (e.g., astaxanthin, fucoxanthin, lutein, zeaxanthin, capsanthin, β-cryptoxanthin, violaxanthin, and the like), and hydroxyl- or carboxyl-derivatives thereof. Such crystalline carotenoids may be used singly, or in combination of two or more kinds thereof.

Especially, lycopene is preferable as the crystalline carotenoid since lycopene is kwon to have a very high antioxidant effect, a very high whitening effect, and the like and the addition of lycopene to food products, cosmetics, pharmaceutical raw materials, processed products thereof, and the like has been conventionally demanded, examined, and practiced.

Lycopene (which may be optionally referred to as "lycopene") is a carotenoid of Formula $C_{40}H_{56}$ (molecular weight of 536.87), which belongs to carotene family, a kind of carotenoids. Lycopene is a red dye indicating an absorption maximum at 474 nm (in acetone).

Lycopene may be present in the form of cis- or trans-isomers with respect to conjugated double bonds at the center of the molecule, and examples include an all-trans form, a 9-cis form, and a 13-cis form, any of which may be available herein.

The carotenoid-containing composition may also contain lycopene in a form of a lycopene-containing oil or a lycopene-containing paste, which is separated and/or extracted from a natural product containing lycopene.

In nature, lycopene is contained in tomato, persimmon, watermelon, and pink grapefruit, and the above-described lycopene-containing oil or paste may be separated and/or extracted from these natural products.

Lycopene may also be the extract, a product produced by further appropriately purifying the extract as needed, or a synthetic product.

In an embodiment, lycopene extracted from tomato is particularly preferable in view of quality and productivity.

A tomato extract, which is widely commercially available, can be used as the lycopene-containing oil or paste, and examples thereof include: LYC-O-MATO (registered trademark) 15% and LYC-O-MATO (registered trademark) 6%, commercially available from Sunbright Co., Ltd.; and LYCOPENE 18 (trade name) commercially available from KYOWA HAKKO BIO CO. LTD.

The crystalline carotenoid may singly compose the carotenoid component, or the crystalline carotenoid and an oil component (oil) used for extracting the crystalline carotenoid from a natural product may compose the carotenoid component in combination.

A content of the crystalline carotenoid in the carotenoid-containing composition is preferably from 0.1 mass % to 5 mass %, more preferably from 0.2 mass % to 4 mass %, and still more preferably from 0.3 mass % to 3 mass %, with respect to a total mass of solid contents (all components excluding water) in the carotenoid-containing composition. In this range, an effect by the crystalline carotenoid can be expected.

The carotenoid component may further contain an amorphous carotenoid (amorphous carotenoid) derived from a natural origin in addition to the above-described crystalline carotenoids.

[(Poly)glycerol Fatty Acid Ester]

The (poly)glycerol fatty acid ester in the carotenoid-containing composition is a (poly)glycerol fatty acid ester that contains from one to six glycerol units and from one to six fatty acid units and has at least one hydroxyl group derived from a glycerol unit.

In such a substance in which the (poly)glycerol fatty acid ester and the crystalline carotenoid are co-dissolved, recrystallization of the crystalline carotenoid can be suppressed.

A (poly)glycerol fatty acid ester containing six or less glycerol units has a high affinity for a carotenoid, while a (poly)glycerol fatty acid ester containing six or less fatty acid units has a high carotenoid crystal suppressing effect. Crystallization of a carotenoid can be sufficiently suppressed by inclusion of a (poly)glycerol fatty acid ester containing a hydroxyl group derived from a glycerol unit.

The (poly)glycerol fatty acid ester is preferably an ester of glycerol with a number of a glycerol unit(s) (average degree of polymerization) of from 1 to 6, which is more preferably from 1 to 4, with a fatty acid with a number of a fatty acid unit(s) of from 1 to 6, which is more preferably from 1 to 5, and a number of carbon atoms of from 8 to 22 (e.g., caprylic acid, capric acid, lauric acid, myristic acid, palmitic acid, stearic acid, oleic acid, linoleic acid, and behenic acid), which is more preferably a fatty acid having from 14 to 18 carbon atoms, from the viewpoint of suppression of recrystallization and the like.

A molecular weight of these (poly)glycerol fatty acid esters is 10000 or less, more preferably 3000 or less, and still more preferably 2500 or less, from the viewpoint of uniform solubility during co-dissolution. Further, an HLB of these (poly)glycerol fatty acid esters preferably have 9 or less, and more preferably 6 or less, from the viewpoint of an affinity for a carotenoid.

In a case in which the carotenoid-containing composition is prepared as a carotenoid-containing powdery composition, the (poly)glycerol fatty acid ester is preferably solid at ordinary temperature from the viewpoint of a carotenoid concentration in the carotenoid-containing powdery composition and an yield from hot-air drying in production of the composition. In other words, increase in an amount of an encapsulating agent is not needed, and a sufficient amount of carotenoid can be contained, in a case in which the (poly) glycerol fatty acid ester is solid at ordinary temperature. Further, in a case in which the (poly)glycerol fatty acid ester is solid at ordinary temperature, the carotenoid-containing powdery composition may hardly adhere to a contact surface during hot-air drying, and reduction in the yield of the carotenoid-containing powdery composition can be suppressed.

Examples of such a (poly)glycerol fatty acid ester that is solid at ordinary temperature include glyceryl myristate, glyceryl monostearate, glyceryl distearate, diglyceryl monostearate, tetraglyceryl monostearate, tetraglyceryl tristearate, tetraglyceryl pentastearate, hexaglyceryl monostearate, hexaglyceryl tristearate, hexaglyceryl tetrabehenate, and hexaglyceryl pentastearate, in which a branch and/or an unsaturated bond are not present in carbon in a fatty acid.

Examples of (poly)glycerol fatty acid esters that can be used in the carotenoid-containing composition include glyceryl myristate, glyceryl monostearate, diglyceryl monostearate, triglyceryl monostearate, pentaglyceryl monoglycerate, hexaglyceryl pentastearate, triglyceryl dipalmitate, glyceryl distearate, tetraglyceryl tristearate, tetraglyceryl pentastearate, hexaglyceryl monostearate, hexaglyceryl tristearate, and hexaglyceryl tetrabehenate. Glyceryl myristate, glyceryl monostearate, diglyceryl monostearate, tetraglyceryl pentastearate, hexaglyceryl pentastearate, tetraglyceryl tristearate, and hexaglyceryl tristearate are preferable from the viewpoint of the suppression of recrystallization and uniform solubility.

A content (mass) of the (poly)glycerol fatty acid ester in the carotenoid-containing composition is preferably from 0.01 times to 9 times, more preferably from 0.1 times to 8 times, and still more preferably from 0.3 times to 5 times, a total content (total mass) of the crystalline carotenoid, from the viewpoint of the stability of the carotenoid-containing composition, while it depends on the kind or content of the crystalline carotenoid that is used.

A sufficient crystal suppressing effect can be expected in a case in which the total mass of the polyglycerol fatty acid ester in the carotenoid-containing composition is 0.01 times the total mass of the crystalline carotenoid, while increase in particle diameters of dispersed particles in an emulsion (hereinafter also referred to as "emulsified particles") can be suppressed in a case in which it is 9 times or less.

[Fatty Acid Ester Component]

The fatty acid ester component in the carotenoid-containing composition is a fatty acid ester component which is at least one selected from the group consisting of a triester of glycerol and fatty acids and an ester of an alcohol having one hydroxyl group and a fatty acid, contains no hydroxyl group in a molecule, and has from 10 to 60 carbon atoms in total.

Such a fatty acid ester component may reduce a dissolution temperature of the crystalline carotenoid. Further, in a case in which the carotenoid-containing composition is an oil-in-water emulsion composition, the fatty acid ester component can allow the fineness of the emulsified particles to be stably kept.

Increase in the particle diameters of dispersed particles in an emulsion cannot be suppressed in a case in which the fatty acid ester component has nine or less carbon atoms in total. A dissolution temperature of the crystalline carotenoid cannot be sufficiently reduced in a case in which the total number of carbon atoms of 61 or more.

The fatty acid ester component preferably has from 10 to 60 carbon atoms in total, and more preferably from 27 to 57 carbon atoms in total, from the viewpoint of reduction in a dissolution temperature of the crystalline carotenoid.

Each fatty acid unit in the fatty acid ester component is preferably a fatty acid unit having from 8 to 18 carbon atoms, more preferably a fatty acid unit having from 8 to 12 carbon atoms, and still more preferably a fatty acid unit having from 8 to 10 carbon atoms, from the viewpoint of suppressing increase in particle diameters of the dispersed particles in an emulsion.

The triester of glycerol and fatty acids preferably has from 10 to 60 carbon atoms in total, and more preferably from 27 to 57 carbon atoms in total, from the viewpoint of reducing a dissolution temperature of the crystalline carotenoid.

Each of three fatty acid units in the triester of glycerol and fatty acids is preferably a fatty acid unit having from 8 to 18 carbon atoms, more preferably a fatty acid unit having from 8 to 12 carbon atoms, and still more preferably a fatty acid unit having from 8 to 10 carbon atoms, from the viewpoint of suppressing increase in particle diameters of dispersed particles in an emulsion. The fatty acid unit may be a fatty acid unit derived from a saturated fatty acid, or may be a fatty acid unit derived from an unsaturated fatty acid. The fatty acid unit may be a fatty acid unit derived from a straight-chain fatty acid, or may be a fatty acid unit derived from a branched-chain fatty acid. Especially, the fatty acid unit is preferably a fatty acid unit derived from a straight-chain fatty acid from the viewpoint of reducing a dissolution temperature of the crystalline carotenoid.

Specific examples of the triester of glycerol and fatty acids include glyceryl tricaprylate, glyceryl tricaprate, glyceryl trilaurate, glyceryl trimyristate, glyceryl tripalmitate, glyceryl tripalmitoleate, glyceryl tristearate, glyceryl trioleate, glyceryl trilinoleate, glyceryl trilinolenate, and glyceryl tri(caprylate/caprate).

Glyceryl tricaprylate, glyceryl tricaprate, glyceryl trilaurate, glyceryl tri(caprylate/caprate), and the like are preferable from the viewpoint of reducing a dissolution temperature of the crystalline carotenoid.

The triester of glycerol and fatty acids may be used singly, or in combination of two or more kinds thereof.

Olive oil, coconut oil, camellia oil, macadamia nut oil, castor oil, avocado oil, evening primrose oil, turtle oil, corn oil, mink oil, rapeseed oil, yolk oil, sesame oil, persic oil, wheat germ oil, sasanqua oil, linseed oil, cotton seed oil, *perilla* oil, soybean oil, peanut oil, tea seed oil, kaya oil, rice bran oil, china wood oil, Japan tung oil, jojoba oil, germ oil, glycerol trioctanoate, glycerol triisopalthymate, salad oil, safflower oil (*Carthamus tinctorius* oil), palm oil, almond oil, hazelnut oil, walnut oil, grape seed oil, cacao oil, shortening, and the like, which are mixtures of the triesters of glycerol and fatty acids, can also be used.

The ester of an alcohol having one hydroxyl group and a fatty acid preferably has from 10 to 50 carbon atoms in total, and more preferably from 10 to 30 carbon atoms in total, from the viewpoint of suppressing increase in particle diameters of dispersed particles in an emulsion.

The fatty acid unit in the ester of an alcohol having one hydroxyl group and a fatty acid is preferably a fatty acid unit having from 8 to 18 carbon atoms, more preferably a fatty acid unit having from 8 to 12 carbon atoms, and still more preferably a fatty acid unit having from 8 to 10 carbon atoms, from the viewpoint of reducing a dissolution temperature of the crystalline carotenoid. The fatty acid unit may be a fatty acid unit derived from a saturated fatty acid, or may be a fatty acid unit derived from an unsaturated fatty acid. The fatty acid unit may be a fatty acid unit derived from a straight-chain fatty acid, or may be a fatty acid unit derived from a branched-chain fatty acid. Especially, the fatty acid unit is preferably a fatty acid unit derived from a straight-chain fatty acid from the viewpoint of reducing a dissolution temperature of the crystalline carotenoid.

The alcohol unit in the ester an alcohol having one hydroxyl group and a fatty acid is preferably an alcohol unit having from 2 to 35 carbon atoms, more preferably an alcohol unit having from 4 to 20 carbon atoms, and still more preferably an alcohol unit having from 5 to 15 carbon atoms, from the viewpoint of reducing a dissolution temperature of the crystalline carotenoid. The alcohol unit may be an alcohol unit derived from a saturated alcohol, or may be an alcohol unit derived from an unsaturated alcohol. The alcohol unit may be an alcohol unit derived from a straight-chain alcohol, or may be an alcohol unit derived from a branched-chain alcohol. Especially, the alcohol unit is preferably an alcohol unit derived from a straight-chain alcohol from the viewpoint of reducing a dissolution temperature of the crystalline carotenoid.

Examples of the ester of an alcohol having one hydroxyl group and a fatty acid include hexyl caprylate, hexyl laurate, methylheptyl laurate, octyldodecyl myristate, methylheptyl isostearate, isocetyl isostearate, methylheptyl isostearate, isopropyl isostearate, butyl stearate, and 2-ethylhexyl stearate. Methylheptyl laurate, methylheptyl isostearate, and the like are preferable from the viewpoint of reducing a dissolution temperature of the crystalline carotenoid.

The ester of an alcohol having one hydroxyl group and a fatty acid may be used singly, or in combination of two or more kinds thereof.

The fatty acid ester component may be used in combination of two or more kinds thereof regardless of the kinds of the triester of glycerol and fatty acids and the ester of an alcohol having one hydroxyl group and a fatty acid.

The content (mass) of the fatty acid ester component is preferably from 3 times to 300 times, more preferably from 5 times to 200 times, and still more preferably from 7 times to 100 times, a total content of the carotenoid component, based on mass, from the viewpoint of reducing a dissolution temperature of the crystalline carotenoid in the carotenoid-containing composition, while it depends on the kind or content of the crystalline carotenoid that is used.

A more favorable crystal suppressing effect can be expected in a case in which a total content of the fatty acid ester component in the carotenoid-containing composition is 3 times or more the total content of the carotenoid component based on mass. In contrast, the carotenoid component in sufficient amount can be blended in the case of 300 times or less.

A content (mass) of the fatty acid ester component, depending on the kind or content of a (poly)glycerol fatty acid ester that is used, is preferably from 0.8 times to 750 times, more preferably 1 time to 300 times, and still more preferably 2 times to 100 times, a total content of the (poly)glycerol fatty acid ester, based on mass, from the viewpoint of the stability of the carotenoid-containing composition.

The stability of the carotenoid-containing composition is improved in a case in which the total content of the fatty acid ester component in the carotenoid-containing composition is 0.8 times or more the total content of the (poly)glycerol fatty acid ester, based on mass, while a sufficient amount of the carotenoid component can be blended in the case of 750 times or less.

In view of the crystallization suppression and stability of the carotenoid component, it is preferable that the fatty acid ester component is a triester of glycerol and fatty acids, a content (mass) of the fatty acid ester component is from 7 times to 100 times a content (mass) of the crystalline carotenoid, a total mass of the polyglycerol fatty acid ester is from 0.3 time to 5 times the content (mass) of the crystalline carotenoid, and the content (mass) of the fatty acid ester component is from 2 times to 100 times a total content of the (poly)glycerol fatty acid ester, based on mass.

[Antioxidant]

The carotenoid-containing composition contains an antioxidant.

It is presumed that decomposition of the crystalline carotenoid (e.g., oxidative decomposition) by heating can be reliably suppressed by incorporating the antioxidant into the carotenoid-containing composition.

The antioxidant may be any one as long as it functions as an antioxidant, of various antioxidants described in "Theory and Practice of Antioxidant" (Kajimoto, San Shobo, 1984) and "Antioxidant Handbook" (Saruwatari, Nishino, Tabata, TAISEISHA LTD., 1976), and is specifically preferably at least one selected from the group consisting of a compound having a phenolic hydroxyl group and an ascorbic acid compound. Preferable examples of preferable the antioxidant will be described below, and the invention is not limited thereto.

Examples of the compound having a phenolic hydroxyl group include aromatic carboxylic acids, cinnamic acids, ellagic acids, BHT (butylated hydroxytoluene), BHA (butylated hydroxyanisole), and vitamin E.

Examples of the aromatic carboxylic acids include gallic acid (3,4,5-hydroxybenzoic acid) and derivatives thereof. Examples of the derivatives of gallic acid (3,4,5-hydroxybenzoic acid) include gallic acid esters such as propyl gallate, epicatechin gallate, and epigallocatechin gallate, and gallic acid glucosides such as gallotannin.

Examples of the cinnamic acids include ferulic acid, chlorogenic acid, and derivatives thereof. Examples of the derivatives of ferulic acid and chlorogenic acid include ferulic acid esters. Specific examples thereof include ferulic acid, γ-orizanol (rice bran extract), caffeic acid (coffeic acid or 3,4-dihydroxycinnamic acid), chlorogenic acid, glyceryl ferulate, and dihydroferulic acid.

Examples of the ellagic acids include ellagic acid.

Examples of the vitamin E include, but are not limited to, those selected from the compound group consisting of tocopherols and derivatives thereof, and the compound group consisting of tocotrienols and derivatives thereof. The vitamin E may be used singly, or in combination of plural kinds thereof. Vitamin E selected from the compound group consisting of tocopherols and derivatives thereof, and the compound group consisting of tocotrienols and the derivatives thereof may also be used in combination.

Examples of the compound group consisting of tocopherols and derivatives thereof include dl-α-tocopherol, dl-β-tocopherol, dl-γ-tocopherol, dl-δ-tocopherol, acetic acid dl-α-tocopherol, nicotinic acid-dl-α-tocopherol, linoleic acid-dl-α-tocopherol, and succinic acid dl-α-tocopherol. Of the compound group consisting of tocopherols and derivatives thereof, dl-α-tocopherol, dl-β-tocopherol, dl-γ-tocopherol, dl-δ-tocopherol, and mixtures thereof (mixed tocopherols) are more preferable. As the tocopherol derivatives, carboxylic acid esters thereof, particularly acetic acid esters, are preferably used.

Examples of the compound group consisting of tocotrienols and derivatives thereof include α-tocotrienol, β-tocotrienol, γ-tocotrienol, and δ-tocotrienol. As the tocotrienol derivatives, acetic acid esters thereof are preferably used.

The compound having a phenolic hydroxyl group is preferably a cinnamic acid from the viewpoint of the stability of the carotenoid component, especially more preferably ferulic acid, γ-orizanol, or a mixture thereof.

The compound having a phenolic hydroxyl group preferably has a low molecular weight, e.g., preferably a molecular weight of from 100 to 3000, and more preferably a molecular weight of from 100 to 1000, from the viewpoint of the stability of the carotenoid component.

A total content of the compound having a phenolic hydroxyl group in the carotenoid-containing composition may be an amount effective for suppressing decomposition or disappearance of the carotenoid component, and may be from 1.3 times to 15.0 times a content of the carotenoid component by mol, preferably from 2 times to 10 times by mol, and more preferably from 3 times to 8 times by mol. The effect of suppressing decomposition or disappearance/deterioration of the carotenoid component is sufficiently exhibited in a case in which the total content of the compound having a phenolic hydroxyl group is 1.3 times or more the content of the carotenoid component by mol, while the blending of a sufficient amount of the carotenoid component is not impaired in the case of 15.0 times or less by mol.

The ascorbic acid compound include ascorbic acids, ascorbic acid esters, and salts thereof.

Examples of the ascorbic acid compound include L-ascorbic acid, sodium L-ascorbate, potassium L-ascorbate, calcium L-ascorbate, L-ascorbic phosphate, L-ascorbic phosphate magnesium salt, L-ascorbic sulfate, L-ascorbic sulfate disodium salt, L-ascorbic stearate, L-ascorbic 2-glucoside, L-ascorbyl palmitate, and L-ascorbyl tetraisopalmitate; and fatty acid esters of ascorbic acids, such as L-ascorbyl stearate, L-ascorbyl tetraisopalmitate, and L-ascorbyl palmitate. Of these, L-ascorbic acid, sodium L-ascorbate, calcium L-ascorbate, L-ascorbic stearate, L-ascorbic 2-glucoside, L-ascorbyl palmitate, L-ascorbic phosphate magnesium salt, L-ascorbic sulfate disodium salt, and L-ascorbyl tetraisopalmitate are particularly preferable from the viewpoint of the suppression of the loss of a carotenoid due to heat.

The ascorbic acid compound may be contained as a simple substance in an oil phase component mixture liquid, or may be blended in a form of an aqueous solution in an oil phase component mixture liquid. A concentration of an ascorbic acid compound in such an aqueous solution is, without particular limitation, generally preferably from 0.05 mass % to 5 mass % from the viewpoint of antioxidation.

A total content of the ascorbic acid compound in the carotenoid-containing composition is preferably from 0.05 time to 50 times, more preferably from 1 time to 10 times, still more preferably from 1.5 times to 10 times, and even more preferably from 2 times to 10 times, a mass of the carotenoid component, from the viewpoint of suppression of loss of the carotenoid component due to heat. The effect of suppressing reduction in a content of the crystalline carotenoid is sufficiently exhibited in a case in which the mass of the ascorbic acid compound is 0.05 time or more the mass of the crystalline carotenoid, while the blending of the sufficient amount of the crystalline carotenoid is not impaired in the case of 50 times or less.

In the carotenoid-containing composition, the antioxidants may be used singly, or in combination of two or more kinds thereof.

By using the compound having a phenolic hydroxyl group together with the ascorbic acid compound as the antioxidant, decomposition due to heating of the carotenoid component (e.g., oxidative decomposition or the like) can be surely suppressed, and decrease of the carotenoid component in producing of the carotenoid-containing composition can be suppressed.

[Additional Oil Components]

The carotenoid-containing composition may contain an additional oil component which is typically used as an oil phase component in addition to each oil phase component described above.

As the additional oil component, which is not particularly limited as long as the component is not dissolved in an aqueous medium but is dissolved in an oil medium, the component having physical properties and functionality depending on the purpose can be appropriately selected and used. For example, amorphous carotenoids, unsaturated fatty acids, squalane, squalene, and the like are preferably used.

Examples of unsaturated fatty acids include monovalent highly unsaturated fatty acids (such as ω-9 and oleic acid) and polyvalent highly unsaturated fatty acids (ω-3, ω-6), each of which having 10 or more, and preferably from 18 to 30, carbon atoms. Such unsaturated fatty acids may be any of known unsaturated fatty acids, and examples of ω-3 oils or fats may include linolenic acid, eicosapentaenoic acid (EPA), and docosahexaenoic acid (DHA) as well as fish oils containing these.

Examples of the ubiquinones include coenzymes Q such as coenzyme Q10.

Examples of fat-soluble vitamins also include fatty acid esters of erythorbic acid, such as erythorbyl palmitate ester and erythorbyl tetraisopalmitate ester; and fatty acid esters of vitamin $B_6$, such as pyridoxine dipalmitate, pyridoxine tripalmitate, pyridoxine dilaurate, and pyridoxine dioctanoate.

[Oil-in-Water Emulsion Composition]

Preferable embodiments of the carotenoid-containing composition include an oil-in-water emulsion composition containing dispersed particles having an average particle diameter in a range of from 30 nm to 100 nm and containing the carotenoid component (hereinafter also referred to as an "oil-in-water emulsion composition").

The oil-in-water emulsion composition contains dispersed particles containing the carotenoid component. Therefore, the oil-in-water emulsion composition is excellent in the fineness stability and transparency of the dispersed particles.

In a case in which the carotenoid-containing composition is an emulsion composition, an average particle diameter of the dispersed particles containing the carotenoid component is preferably from 30 nm to 100 nm from the viewpoint of transparency and from the viewpoint of absorptivity, and is more preferably from 35 nm to 85 nm, and most preferably from 40 nm to 70 nm, from the viewpoint of transparency.

A method of measuring the average particle diameter of the dispersed particles is preferably a dynamic light scattering method in view of a particle diameter range and measurement easiness. Examples of commercially-available measuring apparatuses using the dynamic light-scattering method include a NANOTRAC UPA (trade name, manufactured by NIKKISO CO., LTD.), a dynamic light-scattering method particle size distribution measuring apparatus LB-550 (trade name, manufactured by HORIBA, Ltd.), and a concentrated system particle size analyzer FPAR-1000 (trade name, manufactured by Otsuka Electronics Co., Ltd.). Herein, a value obtained by measurement using the particle size analyzer FPAR-1000 (mentioned above) at 25° C. is adapted as the particle size. Specifically, in the case of an oil-in-water emulsion composition, the oil-in-water emulsion composition is diluted with pure water so that a concentration of an oil phase is set to 0.15 mass %, while in the case of a powdery composition, the powdery composition is diluted with pure water so that a solid concentration thereof is set to 1 mass %, and then the particle diameter is determined therefor in terms of median diameter (d=50) using the particle diameter analyzer FPAR-1000 (mentioned above).

In the case of an emulsion composition, a content of the oil phase composition in the emulsion composition is preferably from 0.1 mass % to 50 mass %, more preferably from 0.5 mass % to 30 mass %, and still more preferably from 3 mass % to 25 mass %, with respect to a total content of the emulsion composition, based on mass, from the viewpoint of exhibiting the function of an oil component.

In the case of the oil-in-water emulsion composition, an emulsifier that can be used as an oil phase component, as well as the above-described components may be contained. Examples of such an emulsifier that can be used as the oil phase component include emulsifiers, described below, with an HLB of 7 or less.

[Aqueous phase Composition]

It is preferable that the aqueous phase composition is formed from an aqueous medium, particularly water, and contains at least an emulsifier.

The emulsifier may be any of an anionic surfactant, a cationic surfactant, an amphoteric surfactant, and a nonionic surfactant.

The emulsifier preferably has an HLB of 10 or more, and more preferably 12 or more, from the viewpoint of an emulsifying property. When HLB is too low, the emulsifying property may become insufficient. An emulsifier having an HLB of from 5 to less than 10 may be further used in combination from the viewpoint of a foam suppressing effect.

As used herein, HLB is a hydrophilicity-hydrophobicity balance typically used in the field of surfactants and can be calculated using a generally used calculation equation such as Kawakami equation. Kawakami equation is shown below.

$$HLB=7+11.7 \log(M_w/M_o)$$

Herein, $M_w$ represents a molecular weight of a hydrophilic group, and $M_o$ represents a molecular weight of a hydrophobic group.

HLB values described in a catalog or the like may also be used.

As is understood from the above-described equation, an emulsifier having an arbitrary HLB value can be obtained by utilizing the additivity of HLB.

A content of the emulsifier in the oil-in-water emulsion composition generally depends on a form of the composition. In a case in which the form is an emulsion composition, the content is preferably from 0.5 mass % to 30 mass %, more preferably from 1 mass % to 20 mass %, and still more preferably from 2 mass % to 15 mass %, with respect to a total content of the composition based on mass. In a case in which the form is a powdery composition, the content is preferably from 0.1 mass % to 50 mass %, more preferably from 5 mass % to 45 mass %, and still more preferably from 10 mass % to 30 mass %, based on a total of the composition. The content within the ranges is preferable in view of easily reducing the interfacial tension between an oil phase and a poor solvent phase, regulating an amount of the emulsifier to be non-excessive, and making problems such as severe foaming of the dispersed composition to hardly occur.

The emulsifier can be used so that a total mass of the emulsifier is in a range of from 0.1 time to 10 times a total mass of an oil component containing the carotenoid component in any form of the powdery composition and the emulsion composition, preferably from 0.5 time to 8 times, and particularly preferably from 0.8 time to 5 times, in view of refining of dispersed particles and the suppression of foaming. In a case in which the mass is within the ranges, the dispersion stability of the composition can be made to be favorable.

Of the emulsifiers, a nonionic surfactant is preferable due to its low-irritating property, low impact on the environment, and the like. Examples of the nonionic surfactant include sucrose fatty acid esters, polyglycerol fatty acid esters, organic acid monoglycerides, propylene glycol fatty acid esters, polyglycerol condensed ricinoleic acid esters, sorbitan fatty acid esters, and polyoxyethylene sorbitan fatty acid esters.

In the sucrose fatty acid ester, a number of carbon atoms in a fatty acid included in the sucrose fatty acid ester is preferably from 12 to 20, and more preferably from 14 to 16, from the viewpoint of the stability of dispersed particles in the composition.

Preferable examples of the sucrose fatty acid ester include sucrose dioleate ester, sucrose distearate ester, sucrose dipalmitate ester, sucrose dimyristate ester, sucrose dilaurate ester, sucrose monooleate ester, sucrose monostearate ester, sucrose monopalmitate ester, sucrose monomyristate ester, and sucrose monolaurate ester, and, of these, sucrose monooleate ester, sucrose monostearate ester, sucrose monopalmitate ester, sucrose monomyristate ester, and sucrose monolaurate ester are more preferable.

These sucrose fatty acid esters may be used singly, or by mixing.

The aqueous phase composition may contain a polyglycerol fatty acid ester in addition to the defined polyglycerol fatty acid ester.

Examples of such a polyglycerol fatty acid ester include esters of polyglycerols having an average degree of polymerization of 2 or more, preferably from 6 to 15, more preferably from 8 to 10, with fatty acids having from 8 to 18 carbon atoms, such as caprylic acid, capric acid, lauric acid, myristic acid, palmitic acid, stearic acid, oleic acid, and linoleic acid.

Preferable examples of the polyglycerol fatty acid ester include hexaglyceryl monooleate ester, hexaglyceryl monostearate ester, hexaglyceryl monopalmitate ester, hexaglyceryl monomyristate ester, hexaglyceryl monolaurate ester, decaglyceryl monooleate ester, decaglyceryl monostearate ester, decaglyceryl monopalmitate ester, decaglyceryl monomyristate ester, and decaglyceryl monolaurate ester.

Of these, decaglyceryl monooleate ester (HLB=12), decaglyceryl monostearate ester (HLB=12), decaglyceryl monopalmitate ester (HLB=13), decaglyceryl monomyristate ester (HLB=14), decaglyceryl monolaurate ester (HLB=16), and the like are more preferable.

These polyglycerol fatty acid esters may be used singly, or by mixing.

The sorbitan fatty acid ester is preferably a fatty acid ester in which a fatty acid has 8 or more carbon atoms, and more preferably 12 or more carbon atoms. Preferable examples of the sorbitan fatty acid ester include sorbitan monocaprylate, sorbitan monolaurate, sorbitan monostearate, sorbitan sesquistearate, sorbitan tristearate, sorbitan isostearate, sorbitan sesquiisostearate, sorbitan oleate, sorbitan sesquioleate, and sorbitan trioleate.

These sorbitan fatty acid esters may be used singly, or by mixing.

The polyoxyethylene sorbitan fatty acid ester is preferably a fatty acid ester whose fatty acid has 8 or more carbon atoms, more preferably 12 or more carbon atoms. A length (a number of added moles) of ethylene oxide in polyoxyethylene is preferably from 2 to 100, and more preferably from 4 to 50.

Preferable examples of the polyoxyethylene sorbitan fatty acid ester include polyoxyethylene sorbitan monocaprylate, polyoxyethylene sorbitan monolaurate, polyoxyethylene sorbitan monostearate, polyoxyethylene sorbitan sesquistearate, polyoxyethylene sorbitan tristearate, polyoxyethylene sorbitan isostearate, polyoxyethylene sorbitan sesquiisostearate, polyoxyethylene sorbitan oleate, polyoxyethylene sorbitan sesquioleate, polyoxyethylene sorbitan trioleate, and the like.

These polyoxyethylene sorbitan fatty acid esters may be used singly, or by mixing.

A phospholipid such as lecithin may also be contained as the emulsifier.

Herein, the phospholipid contains a glycerine backbone as well as a fatty acid residue and a phosphate residue as essential components, to which a base, a polyhydric alcohol, and the like are bound, and is also referred to as lecithin. The phospholipid has a hydrophilic group and a hydrophobic group in the molecule and, therefore, has been conventionally widely used as an emulsifier in the fields of food products, pharmaceutical products, and cosmetics, Lecithin having a purity of 60% or more is industrially utilized as the lecithin and can also be used in the invention. From the viewpoint of formation of a fine oil droplet particle diameter and the stability of a functional oil component, the lecithin is preferably one that is generally referred to as a high-purity lecithin, which has a lecithin purity of 80% or more, and more preferably 90% or more.

Examples of the phospholipid include conventionally known various phospholipids extracted and separated from the living bodies of plants, animals, and microorganisms.

Specific examples of such phospholipids include various lecithins derived from, e.g., plants such as soybean, corn, peanut, rapeseed, and wheat, animals such as yolk and cattle, and microorganisms such as *Escherichia coli*.

Examples of compound names of such lecithins include glycerolecithins such as phosphatidic acid, phosphatidylglycerin, phosphatidylinositol, phosphatidylethanolamine, phosphatidylmethylethanolamine, phosphatidylcholine, phosphatidylserine, bisphosphatidic acid, and diphosphatidylglycerin (cardiolipin); and sphingolecithins such as sphingomyelin.

Besides the above-described high-purity lecithin, a hydrogenated lecithin, an enzyme-degraded lecithin, an enzyme-degraded hydrogenated lecithin, a hydroxylecithin, or the like can be used. These lecithins may be used singly, or in a form of a mixture of a plurality of kinds thereof.

The carotenoid-containing composition includes an oil-in-water emulsion composition obtained by emulsification-mixing the above-mentioned aqueous phase composition with an oil phase composition including an oil phase component, as well as a powdery composition obtained by drying the oil-in-water emulsion composition.

In the case of the powdery composition, a content of the oil phase composition in the powdery composition is preferably from 10 mass % to 50 mass %, more preferably from 10 mass % to 40 mass %, and still more preferably from 10 mass % to 30 mass %, with respect to a total mass of the powdery composition, from the viewpoint of exhibiting the function of an oil component.

In a case in which the carotenoid-containing composition is a powdery composition, the carotenoid-containing composition preferably contains a water-soluble encapsulating agent to protect an oil droplet during a powderization process in drying or during storage of a powder. Thereby, an oil droplet particle diameter can be maintained in a fine state, and deterioration of the carotenoid component in an oil droplet can be reduced.

In a case in which a powdery composition is re-dissolved in water, the water-soluble encapsulating agent enables water-dispersibility of an oil component to be favorable, and also enables transparency after the re-dissolution to be favorable.

The water-soluble encapsulating agent is preferably a polysaccharide which is at least one selected from a fruit sugar-polymer or oligomer including a saccharide unit containing at least two fruit sugar units (hereinafter simply referred to as a "fruit sugar-polymer or oligomer").

The fruit sugar-polymer or oligomer refers to a polymer or an oligomer that contains a fruit sugar (fructose) as a repeating unit and includes a saccharide unit in which a plurality of saccharide units is bound by dehydration condensation. As used herein, the fruit sugar-polymer or oligomer having less than 20 repeating units of a saccharide including a fruit sugar unit is referred to as a fruit sugar oligomer, and the fruit sugar-polymer or oligomer having the 20 or more repeating units is referred to as a fruit sugar polymer.

The number of the saccharide repeating units is preferably from 2 to 60, and more preferably from 4 to 20, from the viewpoint of suitability to drying and oil droplet refining at re-dissolution. In a case in which the number of repeating units (polymerization degree of fruit sugar) is two or more, water vapor absorption is not too strong, and a reduction of recovery rate due to adherence to a drying container in a drying process can be effectively prevented, while in a case in which the number is 60 or less, coarsening of an oil droplet particle diameter during re-dissolving to water can be effectively prevented.

The fruit sugar-polymer or oligomer may also contain an additional monosaccharide as well as a fruit sugar in a molecular terminal or chain. Examples of the additional monosaccharide unit that can be contained include, but are not limited to, glucose (glucose), galactose, mannose, idose, altrose, gulose, talose, allose, xylose, arabinose, lyxose, ribose, threose, erythrose, erythrulose, xylulose, ribulose, psicose, sorbose, and tagatose. Of these monosaccharides, glucose is preferable from the viewpoint of easy availability. A bonding site of the additional monosaccharide unit is preferably at a terminal of the fruit sugar chain from the viewpoint of refining of oil droplets at re-dissolution.

In a case in which the fruit sugar-polymer or oligomer contains a saccharide other than fruit sugar, a content ratio thereof is 50% or less, preferably 30% or less, by polymerization degree, with respect to a number of fruit sugar units in the fruit sugar-polymer or oligomer, from the viewpoint of drying suitability and the refining of oil droplets at re-dissolving.

Examples of a water-soluble encapsulating agent preferably used from the viewpoint of storage stability of a dye, easy availability, and the like include inulins. An inulin refers to a fruit sugar polymer or fruit sugar oligomer having one glucose at a terminal. Inulins are known to be present widely in the natural world and are contained abundantly in *Cichorium endivia, Jerusalem artichoke*, dahlia, garlic, leek, onion, and the like. The details of inulins are described in Handbook of Hydrocolloids, G. O. Phillips, P. A. Williams Ed., 397-403, (2000) CRC Press. Generally, a chain length is expressed by using G for representing a glucose unit, and F for representing a fruit sugar unit. Herein, the inulins do not contain sucrose, which is represented by GF.

Inulins extracted from natural sources are typically polymers or oligomers ranging from GF2 (kestose), GF3 (nystose), and GF4 (fructosylnystose) to around GF60, or mixtures thereof.

Examples of inulins include commercially available products powdered by condensation and spray-drying of aqueous solutions of inulins separated and hot-water extracted from the roots of *Cichorium endivia*, *Jerusalem artichoke*, dahlia, and the like. Examples thereof include: FRUTAFIT (trade name, manufactured by SENSUS), that is extracted from a root of *Cichorium endivia*; BENEO (trade name, manufactured by ORAFTI), that is extracted from a root of *Cichorium endivia*; a reagent derived from a dahlia root (manufactured by Wako Pure Chemical Industries, Ltd., or manufactured by Sigma Ltd.); and a reagent extracted from a root of *Cichorium endivia* (manufactured by Sigma Ltd.).

The fruit sugar-polymer and oligomer may also include a product that is prepared from sucrose using the metastatic activity of fructan in β-fructofuranosidase. Examples thereof include FUJI FF (trade name, manufactured by Fuji Nihon Seito Corporation) and GF2 (trade name, manufactured by Meiji Seika Kabushiki Kaisha).

In the inulin, the number of repeating units of fruit sugar (polymerization degree) is preferably from 2 to 60 from the viewpoint of the refining of oil droplets at re-dissolution, and the polymerization degree of the fruit sugar is more preferably from 4 to 20 from the viewpoint of adherence to an apparatus during spray-drying and solubility to water.

The fruit sugar-polymer or oligomer is preferably added at the time of emulsification, while a part or all thereof may be added after emulsification.

An additional water-soluble polymer or oligomer may be used in combination with the fruit sugar-polymer or oligomer. Examples of the additional water-soluble polymer or oligomer include, but are not limited to, agarose, starch, carrageenan, gelatin, xanthan gum, gellan gum, galactomannan, casein, tragacanth gum, xyloglucan, β-glucan, curdlan, water-soluble soybean fiber, chitosan, alginic acid, and atrium alginate.

A content of the water-soluble encapsulating agent in the carotenoid-containing composition is preferably from 0.5 time to 50 times, more preferably from 1 time to 20 times, still more preferably from 1 time to 10 times, and even more preferably from 2 times to 5 times, a total mass of an oil component in the composition, based on mass, from the viewpoints of retention of shape and solubility.

The water-soluble encapsulating agent is contained in the aqueous phase of the carotenoid-containing composition. It may also be incorporated as an aqueous phase composition during pressurization-emulsification described below, or may be added to the aqueous phase of the carotenoid-containing composition after the pressurization-emulsification.

[Additional Components]

Besides each component described above, components that are commonly used in the fields of food products, cosmetics, and the like may also be appropriately blended in the carotenoid-containing composition depending on the form of the composition. The additional components may be blended as components of the oil phase component mixture liquid, the carotenoid-containing oil phase composition, or the aqueous phase composition, depending on the properties of the additional components, or may be blended as additional components to the aqueous phase of the carotenoid-containing composition.

Examples of such other components include: polyhydric alcohols such as glycerol and 1,3-butylene glycol; monosaccharides or polysaccharides such as glucose, fruit sugar, milk sugar, malt sugar, cane sugar, pectin, κ-carrageenan, locust bean gum, guar gum, hydroxypropyl guar gum, xanthan gum, karaya gum, tamarind seed polysaccharide, gum arabic, tragacanth gum, hyaluronic acid, sodium hyaluronate, sodium chondroitin sulfate, and dextrin; sugar alcohols such as sorbitol, mannitol, maltitol, lactose, maltotriitol, and xylitol; inorganic salts such as sodium chloride and sodium sulfate; proteins having a molecular weight of more than 5000, such as casein, albumin, methylated collagen, hydrolyzed collagen, water-soluble collagen, and gelatin; synthetic polymers such as carboxyvinyl polymers, sodium polyacrylate, polyvinyl alcohol, polyethylene glycol, and ethylene oxide-propylene oxide block copolymer; water-soluble cellulose derivatives such as hydroxyethyl cellulose methyl cellulose; flavonoids (catechin, anthocyanin, flavone, isoflavone, fravane, flavanone, and rutin); phenolic acids (chlorogenic acid, ellagic acid, gallic acid, and propyl gallate); lignanes; curcumins; and coumarins. These may be contained, based on the functions thereof, for example, as functional components, excipients, viscosity modifiers, radical scavengers, or the like.

In addition, for example, other additives that are typically used for the intended use, such as various medicinal components, pH adjusters, pH buffers, ultraviolet ray absorbers, antiseptic agents, perfumes, and coloring agents, may be used in combination.

In the carotenoid-containing composition, crystallization of the crystalline carotenoid is suppressed, and a desired effect due to the carotenoid can be sufficiently expected. Accordingly, the carotenoid-containing composition can be preferably applied to a food composition, a cosmetic composition, and a pharmaceutical composition.

A component that can be added to food products or cosmetics can be appropriately added to food products or cosmetics containing an oil-in-water emulsion composition, if necessary. Particularly, in a case in which the composition is used in food products, the food can be stored as a powdered food product for a long term, while in a case in which the composition is dissolved in an aqueous medium, the composition becomes a composition containing fine emulsified particles and having excellent transparency.

A food product, a cosmetic, or the like containing the carotenoid-containing composition can exhibit an effect that may be insufficiently exerted due to the presence of the crystal, for example, favorable absorptivity for a carotenoid.

The cosmetic composition is preferably used in, for example, lotion, liquid cosmetics, milky lotion, cream pack mask, pack, shampoo cosmetics, fragrance cosmetics, liquid body cleaning preparations, UV care cosmetics, deodorant cosmetics, oral care cosmetics, and the like.

As the foods, not only common foods such as nutrition-supplement drinks, revitalizers, palatable drinks, and frozen desserts but also tablet-shaped, granule-shaped, and capsule-shaped nutritional supplementary foods, and the like can be preferably used.

In the case of use for functional foods, although the amount of the added powdery composition cannot be simply generally defined because the amount varies depending on the kind and intended use of a product, the powdery composition can be used by adding the powdery composition so as to become in a range of from 0.01 mass % to 10 mass %, preferably from 0.05 mass % to 5 mass %, with respect to the total mass of the product, based on mass. In a case in which the addition amount is 0.01 mass % or more, exertion of an intended effect may be prospective, while in a case in which the addition amount is 10 mass % or less, appropriate effects may be often exerted efficiently.

The carotenoid-containing composition can be produced according to a known method. Examples of preferable methods of producing the carotenoid-containing composition include a production method described below.

[Method of Producing Carotenoid-Containing Composition]

The method of producing a carotenoid-containing composition according to one embodiment of the invention includes heating, under a temperature condition of 90° C. or more, an oil phase component-mixture liquid, the oil phase component mixture liquid containing: a carotenoid component containing at least one crystalline carotenoid; a (poly)glycerol fatty acid ester that contains from one to six glycerol units, from one to six fatty acid units, and at least one hydroxyl group derived from a glycerol unit; a fatty acid ester component which is at least one selected from the group consisting of a triester of glycerol and fatty acids and an ester of an alcohol having one hydroxyl group and a fatty acid, contains no hydroxyl group in a molecule, and has from 10 to 60 carbon atoms in total; and an antioxidant.

In the production method, the carotenoid component containing a crystalline carotenoid is heated together with the defined (poly)glycerol fatty acid ester, the defined fatty acid ester component, and the antioxidant under a temperature condition of not less than the dissolution temperature of the carotenoid component. Therefore, the carotenoid component is co-dissolved together with the defined (poly)glycerol fatty acid ester and the defined fatty acid ester component. By using the carotenoid-containing oil phase composition obtained by the co-dissolution as an oil phase composition to be subjected to heating and emulsifying together with an aqueous phase composition containing a water-soluble emulsifier, the carotenoid-containing composition obtained by the emulsification can become a composition in which the crystallization of the crystalline carotenoid is suppressed.

In the production method, the defined fatty acid ester component is added. As a result, a dissolution temperature of the carotenoid component can be reduced as compared to a case in which the defined fatty acid ester component is not added.

As used herein, the "dissolution temperature of a crystalline carotenoid" and the "dissolution temperature of a carotenoid component (including a crystalline carotenoid)" refer to a temperature at which the crystalline carotenoid begins to liquefy in a case in which a temperature of a mixture containing the components of the oil phase composition including the crystalline carotenoid is gradually increased.

In the production method, first, an oil phase component mixture liquid can be obtained by mixing: a carotenoid component containing at least one crystalline carotenoid; a (poly)glycerol fatty acid ester which contains from one to six glycerol units, from one to six fatty acid units, and at least one hydroxyl group derived from a glycerol unit; a fatty acid ester component which is at least one selected from the group consisting of a triester of glycerol and fatty acids and an ester of an alcohol having one hydroxyl group and a fatty acid, contains no hydroxyl group in a molecule, and has from 10 to 60 carbon atoms in total; and an antioxidant (hereinafter also referred to as an "oil phase component mixing step"). The oil phase component mixture liquid may contain an additional oil phase component, if necessary.

Specific examples, contents and preferable ranges of the crystalline carotenoid, the (poly)glycerol fatty acid ester, the fatty acid ester, the antioxidant, and the additional oil component contained in the oil phase component mixture liquid used in the production method are the same as those described for each component contained in the carotenoid-containing composition.

Then, the carotenoid-containing composition can be obtained by heating the oil phase component mixture liquid under a temperature condition of 90° C. or more (hereinafter also referred to as an "oil phase component heating step"). The heating temperature may be 90° C. or more, and depends on the kind and the like of the crystalline carotenoid or the carotenoid component used. For example, in a case in which the carotenoid-containing composition is prepared using lycopene as the carotenoid component, the heating temperature can be from 90° C. to 155° C., preferably from 110° C. to 150° C., and more preferably from 120° C. to 145° C., from the viewpoint of the suppression of thermal decomposition.

The heating time may be time which allows the carotenoid component to dissolve in the oil phase component mixture liquid, and is preferably from 10 minutes to 60 minutes, and more preferably from 15 minutes to 45 minutes, from the viewpoint of efficiently suppressing an amorphization of the crystal and decomposition of the carotenoid due to excessive heat, while the heating time is not limited thereto.

The carotenoid-containing composition can be obtained from the oil phase component mixture liquid containing a carotenoid component and a polyglycerol fatty acid ester by such a heating treatment.

It is preferable to make the oil phase component mixture liquid in its entirety to have uniform temperature in the heating treatment. Therefore, sufficient stirring while heating is preferable, and it is desirable to maintain a constant temperature with using an airtight container and overheating while stirring.

By the above-described oil phase component heating, the carotenoid-containing composition is obtained as an oil phase composition.

[Method of Producing Emulsion Composition]

In a case in which the carotenoid-containing composition is an emulsion composition, the method may include emulsifying, after the oil phase component heating step, the oil phase composition obtained in the oil phase component heating step and an aqueous phase composition (emulsification step). Thereby, an oil-in-water emulsion composition in which an oil phase component containing a carotenoid component is finely dispersed as oil droplets (emulsified particles) in water can be obtained. In the emulsion composition, the carotenoid component containing a crystalline carotenoid is maintained stably.

Although a ratio (mass standard) between an oil phase and an aqueous phase in the emulsification is not particularly limited, the ratio (mass %) of oil phase/aqueous phase is preferably from 0.1/99.9 to 50/50, more preferably from 0.5/99.5 to 30/70, and still more preferably from 1/99 to 20/80.

By setting the ratio of oil phase/aqueous phase to 0.1/99.9 or more, active components do not become insufficient, which results in a tendency that a practical problem of the oil-in-water emulsion composition is not caused. By setting the ratio of oil phase/aqueous phase to 50/50 or less, a concentration of the emulsifier does not become low, which results in a tendency that emulsion stability of the emulsion composition is not deteriorated.

The pressurization-emulsification may be performed by one step-operation of the emulsification, while it is preferable to perform two or more step-operations of the emulsification, from the viewpoint of obtaining uniform and fine emulsified particles.

Specifically, it is particularly preferable to use a combination of two or more kinds of emulsification devices in a manner such that emulsification is performed by one step-emulsification operation in which emulsification is performed using an ordinary emulsification apparatus utilizing a shearing action (such as a stirrer, impeller stirring, a homomixer, or a continuous-flow type shearing apparatus) followed by emulsification through a high-pressure homogenizer or the like. By using a high-pressure homogenizer, the emulsion can be made to have further uniform and fine particles of droplets. The operation may be performed plural times in order to make the particle diameter of oil droplets more uniform.

Any of generally known emulsification methods such as spontaneous emulsification methods, interfacial chemical emulsification methods, electric emulsification methods, capillary emulsification methods, mechanical emulsification methods, and ultrasonic emulsification methods can be herein used as an emulsification means.

An interfacial chemical emulsification method such as a PIT emulsification method or a gel emulsification method is known as a useful method of making emulsified particles in an emulsion composition finer. This method has an advantage in that consumption energy is low, and therefore the method is suitable in the case of finely emulsifying a material which easily deteriorates by heat.

As a generally-used emulsification method, a method of using a mechanical force is applied, that is, a method of tearing apart oil droplets by applying a shearing force thereto from the outside. High-speed and high-shearing stirring machines are most-general as the mechanical force. Stirring machines which are called homomixers, disperser mixers, and ultra-mixers are commercially available as such stirring machines.

A high-pressure homogenizer is available as another mechanical emulsification apparatus that is useful for particle-size refining, and various kinds of apparatuses thereof are commercially available. The high-pressure homogenizer is capable of applying greater shearing force than a stirring method. Therefore, particle-size reduction can be realized even in a case in which an amount of an emulsifier is relatively small.

There are main types of high-pressure homogenizer: one is a chamber type high-pressure homogenizer having a fixed throttling section, and the other is a homogeneous valve type high-pressure homogenizer in which the divergence of throttle is controlled.

Examples of the chamber type high-pressure homogenizer include MICROFLUIDIZER (trade name, manufactured by Microfluidics Corporation), NANOMIZER (registered trademark, manufactured by Yoshida Kikai Co., Ltd.), and ALTIMIZER (trade name, manufactured by Sugino Machine Limited).

Examples of the homogeneous valve type high-pressure homogenizer include a Gaulin-type homogenizer (manufactured by APV), a Rannie-type homogenizer (manufactured by Rannie), a high-pressure homogenizer (manufactured by Niro Soavi), a homogenizer (manufactured by Sanwa Machinery Trading Co., Ltd.), a high-pressure homogenizer (manufactured by Izumi Food Machinery Co., Ltd.), and an ultrahigh-pressure homogenizer (manufactured by IKA Corporation).

There is an ultrasonic homogenizer as a dispersing apparatus having a relatively favorable energy efficiency and an emulsification apparatus having a simple structure. Examples of high-power ultrasonic homogenizers that can be produced include ULTRASONIC HOMOGENIZER US-600, ULTRASONIC HOMOGENIZER US-1200T, ULTRASONIC HOMOGENIZER RUS-1200T, and ULTRASONIC HOMOGENIZER MUS-1200T (which are trade names, manufactured by Nihonseiki Kaisha Ltd.), and ULTRASONIC PROCESSOR UIP-2000, ULTRASONIC PROCESSOR UIP-4000, ULTRASONIC PROCESSOR UIP-8000, and ULTRASONIC PROCESSOR UIP-16000 (which are trade names, manufactured by Heilscher). These high-power ultrasonic homogenizers are used at a frequency of 25 kHz or less, and preferably at a frequency of from 15 to 20 kHz.

As other known emulsifying means, a method of using an apparatus that does not include an extraneous stirring section and needs only low energy is also useful, and examples of the apparatus include static mixers, micro channels, micro mixers, and membrane emulsification apparatuses.

A temperature condition in the case of emulsification-dispersing is not particularly limited. From the viewpoint of the stability of a functional oil component, it is preferably from 10° C. to 100° C. A preferable range can be appropriately selected depending on the melting point of the functional oil component to be handled.

In the case of using a high-pressure homogenizer, processing is preferably performed at a pressure of 50 MPa or more, more preferably from 50 MPa to 280 MPa, and still more preferably 100 MPa to 280 MPa.

From the viewpoint of keeping the particle size of the emulsified particles, it is preferable that an emulsified liquid that is an emulsion dispersed composition is cooled through some sort of cooling machine within 30 seconds, preferably within 3 seconds immediately after the emulsified liquid has passed through a chamber.

The production method may include drying the oil-in-water emulsion composition obtained in an oil-in-water emulsion composition preparation step to obtain a powdery composition (hereinafter also referred to as a "powderization step"). Thereby, a carotenoid-containing composition can be obtained as a powdery composition. The carotenoid-containing composition as a powdery composition is a composition which has storage stability due to the powderized form and in which crystallization of crystalline carotenoid has been suppressed in the powdery composition as well as the emulsion composition in which the powdery composition has been re-dissolved in an aqueous medium.

As for the drying means used in the powderization step, known drying means may be used, and examples of the drying means include natural drying, heat drying, hot air drying, high-frequency drying, ultrasonic drying, reduced-pressure drying, vacuum drying, freeze drying, and spray drying. These means may be used singly, or in combination of two or more means.

Reduced-pressure drying, vacuum drying, freeze drying, and spray drying are preferable since the carotenoid-containing composition often contains functional materials that are weak against heat. As one of the vacuum drying methods, a method of conducting vacuum (reduced-pressure) drying while keeping a temperature of 0° C. or less but equal to or higher than a freezing temperature is also preferable.

In the case of vacuum drying or reduced-pressure drying, the drying is preferably conducted by repeating concentrating while gradually increasing the degree of pressure reduction in order to avoid scatter of the liquid due to bumping.

In an embodiment, the freeze drying in which ice is sublimated from a material in a frozen state to remove water is preferable. The freeze drying method has a great advantage that since the drying process usually proceeds at 0° C. or less, ordinarily at from around −20° C. to −50° C., heat denaturation of the material is not caused, and in the course of water recovery, taste, color, nutritional value, shape, texture, and the like can be easily restored to their states before the drying.

Examples of the commercially available freeze dryer include, but are not limited to, FREEZE DRYER VD-800F (trade name, manufactured by Taitec Corporation), FLEXI-DRY MP (trade name, manufactured by FTS Systems Inc.), DURATOP/DURASTOP (trade name, manufactured by FTS Systems Inc.), TAKARA VACUUM FREEZE DRYER Model A (trade name, manufactured by Takara ATM), DESKTOP FREEZE-DRYER FD-1000 (trade name, manufactured by Tokyo Rikakikai Co., Ltd.), VACCUM FREEZE-DRYER FD-550 (trade name, manufactured by Tokyo Rikakikai Co., Ltd.), and VACCUM FREEZE-DRYER (manufactured by Takara Seisakusho).

As the drying means, a spray-drying method is particularly preferable from the viewpoint of a balance between production efficiency and quality. The spray drying is a sort of convective-hot air drying. The liquid composition is sprayed as fine particles of several hundred micrometers or less in a hot air and resultantly drops in a tower while being dried, whereby the composition is collected as a solid powder. Though the material is temporarily exposed to hot air, increase of temperature does not become too high because of very short exposure time and vapor latent heat, and therefore heat denaturation of the material does not easily occur and a change due to water recovery is small as is the case with freeze drying. In the case of a material that is very weak against heat, it is also possible to feed cold air instead of hot air. In this case, it is preferable in the point that relatively milder drying can be realized, though the drying performance is reduced.

Examples of the commercially available spray dryer include, but are not limited to, spray dryers: SPRAY DRYER SD-1000 (trade name, manufactured by Tokyo Rikakikai Co., Ltd.), SPRAY DRYER-8i (trade name, manufactured by Ohkawara Kakohki Co., Ltd.), CLOSED SPRAY DRYER CL-12 (trade name, manufactured by Ohkawara Kakohki Co., Ltd.), SPRAY DRYER ADL 310 (trade name, Yamato Scientific Co., Ltd.), MINISPRAY DRYER B-290 (trade name, manufactured by BUCHI), PJ-MiniMax (trade name, manufactured by Powdering Japan), and PHARM-ASD (registered trademark, manufactured by GEA Niro).

It is also preferable to produce granular particles exerting excellent handling ability at the same time as drying by using an apparatus by which both drying and granulation are performed at the same time, such as a fluid-bed granulation dryer MP-01 (trade name, manufactured by POWREX CORPORATION) or a spray dryer with a built-in fluid-bed FSD (trade name, manufactured by GEA Niro).

The powdery composition obtained by the production method according to one embodiment of the invention has a water recovery property, i.e., a property of restoring the state of the oil-in-water emulsion composition prior to drying in a case in which the powdery composition is re-dissolved (re-dispersed) in water again.

The carotenoid-containing composition obtained by the production method can also be used to make an oil-in-water emulsion composition or a powdery composition obtained by powderizing the oil-in-water emulsion composition.

The average particle diameter in the carotenoid-containing composition means a particle diameter of the dispersed particles (oil droplets) in the emulsion composition in a case in which the composition is an oil-in-water emulsion composition, while in a case in which the composition is a powdery composition, it means a particle diameter of the dispersed particles (oil droplets) obtained as a 1 mass % aqueous solution by re-dissolving the powdery composition in water.

The average particle diameter of the dispersed particles may be adjusted by factors such as stirring conditions in the production method (shearing force, temperature, pressure) and ratio between oil phase and aqueous phase, besides the components of the composition.

The average particle diameter of the carotenoid-containing composition obtained by the production method is preferably from 30 nm to 100 nm from the viewpoint of transparency and absorptivity, and more preferably from 35 nm to 85 nm, still more preferably from 40 nm to 70 nm from the viewpoint of transparency.

EXAMPLES

The invention will be described below with reference to examples, but the invention is not limited thereto. The numerical values expressed by "part" or "%" in the following description are based on mass, unless otherwise specified.

Example 1

Preparation of Oil Phase Composition

Of the oil phase components described below, (5) and (3) were mixed and stirred at room temperature, and (2), (1), and (4) were added thereto in this order while mixed and stirred to be dissolved. Then, the mixture was heated for 60 minutes so that a temperature of the mixture became from room temperature to a range of 135° C. to 145° C. while stirring, and the temperature was maintained at a temperature of from 135° C. to 145° C. for 5 minutes, followed by cooling the mixture to room temperature to obtain a carotenoid-containing composition (oil phase composition 1). The melting point of LYCOPENE 18 (mentioned above) is 153° C. (endothermic peak value in DSC measurement).

| Oil phase composition 1 | |
|---|---|
| (1) Lycopene paste (lycopene concentration: 18%)*[1] | 1.00 part |
| (2) Diglyceryl monostearate*[2] | 0.20 part |
| (3) Ferulic acid*[3] | 0.30 part |
| (4) Calcium ascorbate 50% solution*[4] | 0.80 part |
| (5) Glycerol tri(caprylate/caprate)*[5] | 1.30 parts |

*[1]Kyowa Hakko Bio Co. Ltd., trade name "LYCOPENE 18" (molecular weight of 537.0)
*[2]Nikko Chemicals Co., Ltd., "NIKKOL (registered trademark) DGMS" (HLB = 5.0)
*[3]Tsuno Food Industrial Co., Ltd. (molecular weight of 194)
*[4]Molecular weight of 390 (as anhydride)
*[5]Kao Corporation "COCONAD (registered trademark) MT" (HLB = 1)

Examples 2 to 11 and Comparative Examples 1 to 6

In Examples 2 to 11 and Comparative Examples 2 to 6, oil phase compositions 2 to 11 and 13 to 17 were obtained in the same manner as in Example 1 except that the kinds and contents of the oil phase components were changed as listed in Table 1.

In Comparative Example 1, an oil phase composition 12 was obtained in the same manner as in Example 1 except that each oil phase component listed in Table 1 was stirred and mixed while being warmed from room temperature to 70° C. to 80° C., and was maintained at 70° C. to 80° C. for 5 minutes.

As each component in Table 1, the following components were used:
  Glyceryl monostearate: NIKKOL (registered trademark) MGS-F40V Nikko Chemicals Co., Ltd.
  Tetraglyceryl tristearate: NIKKOL (registered trademark) Tetraglyn 3-S Nikko Chemicals Co., Ltd.
  Tetraglyceryl pentastearate: NIKKOL (registered trademark) Tetraglyn 5-S Nikko Chemicals Co., Ltd.
  Hexaglyceryl tristearate: NIKKOL (registered trademark) Hexaglyn 3-S Nikko Chemicals Co., Ltd.
  Hexaglyceryl pentastearate: NIKKOL (registered trademark) Hexaglyn 5-SV Nikko Chemicals Co., Ltd.
  Decaglyceryl monooleate: NIKKOL (registered trademark) Decaglynl-OV Nikko Chemicals Co., Ltd.
  γ-Orizanol: Tsuno Food Industrial Co., Ltd. Co., Ltd. (molecular weight of 602.89)
  Gallic acid: molecular weight of 170.12
  Ascorbyl palmitate: reagent from Wako Pure Chemical Industries, Ltd.
  BHT (dibutyl hydroxytoluene): reagent from Wako Pure Chemical Industries, Ltd.
  Olive oil (mixture of fatty acid triglycerides (about 70% oleic acid, about 10% linoleic acid, about 10% palmitic acid, about 3% stearic acid)): reagent from Wako Pure Chemical Industries, Ltd.

A numerical value indicating the blending amount of each component in Table 1 represents "part(s)".

TABLE 1

| | | Example 1 Oil phase composition 1 | Example 2 Oil phase composition 2 | Example 3 Oil phase composition 3 | Exampe 4 Oil phase composition 4 | Example 5 Oil phase compostion 5 | Example 6 Oil phase composition 6 |
|---|---|---|---|---|---|---|---|
| (1) | Lycopene paste (lycopene content of 18%) | 1.00 | 1.00 | 1.00 | 1.00 | 1.00 | 1.00 |
| (2) | Glyceryl monostearate | | | 0.20 | | | |
| | Diglyceryl monostearate | 0.20 | 1.62 | | | | |
| | Tetraglyceryl tristearate | | | | | | 1.00 |
| | Tetraglyceryl pentastearate | | | | | 0.002 | |
| | Hexaglyceryl tristearate | | | | | | |
| | Hexaglyceryl pentastearate | | | | 0.20 | | |
| | Decaglyceryl monooleate | | | | | | |
| (3) | Ferulic acid | 0.30 | 0.30 | 0.09 | | | |
| | γ-Orizanol | | | | 0.90 | | |
| | Gallic acid | | | | | 0.30 | |
| | Ascorbyl palmitate | | | | | | 0.30 |
| | BHT | | | | | | |
| | Calcium ascorbate (50%) | 0.80 | 0.80 | 0.80 | 0.80 | 0.80 | 0.80 |
| (4) | Glyceryl tri(caprate/caproate) ($C_{8-10}$) | 1.30 | 1.30 | 1.30 | 1.30 | | 0.50 |
| | Glyceryl tricaprate ($C_8$) [COCONAD RK from Kao Corporation] | | | | | | |
| | Methylheptyl laurate ($C_{12}$) [NIKKOL GS-MHL] | | | | | | |
| | Methylheptyl isostearate ($C_{18}$) [NIKKOL GS-MHIS] | | | | | | |
| | Olive oil (main component: $C_{18}$) | | | | | 1.50 | |
| Warming treatment | | | | | | | |
| | Set temperature (° C.) | 135-145 | 135-145 | 135-145 | 135-145 | 135-145 | 135-145 |
| | Heating-up time (min) | 60 | 60 | 60 | 60 | 60 | 60 |
| | Retention time (min) | 5 | 5 | 5 | 5 | 5 | 5 |

| | | Example 7 Oil phase composition 7 | Example 8 Oil phase composition 8 | Example 9 Oil phase composition 9 | Example 10 Oil phase composition 10 | Example 11 Oil phase composition 11 |
|---|---|---|---|---|---|---|
| (1) | Lycopene paste (lycopene content of 18%) | 1.00 | 1.00 | 1.00 | 1.00 | 1.00 |
| (2) | Glyceryl monostearate | | | | | |
| | Diglyceryl monostearate | | 0.10 | 0.20 | 0.20 | 0.20 |
| | Tetraglyceryl tristearate | | | | | |
| | Tetraglyceryl pentastearate | | | | | |
| | Hexaglyceryl tristearate | 0.10 | | | | |
| | Hexaglyceryl pentastearate | | | | | |
| | Decaglyceryl monooleate | | | | | |
| (3) | Ferulic acid | | 0.30 | 0.30 | 0.30 | 0.30 |
| | γ-Orizanol | | | | | |
| | Gallic acid | | | | | |
| | Ascorbyl palmitate | | | | | |
| | BHT | 0.30 | | | | |
| | Calcium ascorbate (50%) | 0.80 | 0.80 | 0.80 | 0.80 | 0.80 |

TABLE 1-continued

| | | | | | | |
|---|---|---|---|---|---|---|
| (4) Glyceryl tri(caprate/caproate) ($C_{8-10}$) | 1.50 | 1.50 | | | | |
| Glyceryl tricaprate ($C_8$) [COCONAD RK from Kao Corporation] | | | 1.30 | | | |
| Methylheptyl laurate ($C_{12}$) [NIKKOL GS-MHL] | | | | 1.30 | | |
| Methylheptyl isostearate ($C_{18}$) [NIKKOL GS-MHIS] | | | | | 1.30 | |
| Olive oil (main component: $C_{18}$) | | | | | | |
| Warming treatment | | | | | | |
| Set temperature (° C.) | 135-145 | 135-145 | 135-145 | 135-145 | 135-145 | |
| Heating-up time (min) | 60 | 60 | 60 | 60 | 60 | |
| Retention time (min) | 5 | 5 | 5 | 5 | 5 | |

| | Comparative Example 1 Oil phase composition 12 | Comparative Example 2 Oil phase composition 13 | Comparative Example 3 Oil phase composition 14 | Comparative Example 4 Oil phase composition 15 | Comparative Examples 5 Oil phase composition 16 | Comparative Examples 6 Oil phase composition 7 |
|---|---|---|---|---|---|---|
| (1) Lycopene paste (lycopene content: 18%) | 1.00 | 1.00 | 1.00 | 1.00 | 1.00 | 1.00 |
| (2) Glyceryl monostearate | | | | | | |
| Diglyceryl monostearate | 1.50 | 1.50 | 0.20 | | | 0.20 |
| Tetraglyceryl tristearate | | | | | | |
| Tetraglyceryl pentastearate | | | | | | |
| Hexaglyceryl tristearate | | | | | | |
| Hexaglyceryl pentastearate | | | | | | |
| Decaglyceryl monooleate | | | | | 1.00 | |
| (3) Ferulic acid | 0.30 | 0.30 | 0.30 | 0.30 | 0.30 | |
| γ-Orizanol | | | | | | |
| Gallic acid | | | | | | |
| Ascorbyl palmitate | | | | | | |
| BHT | | | | | | |
| Calcium ascorbate (50%) | 0.80 | 0.80 | 0.80 | 0.80 | 0.80 | |
| (4) Glyceryl tri(caprate/caproate) ($C_{8-10}$) | | | | 1.50 | 1.30 | 1.50 |
| Glyceryl tricaprate ($C_8$) [COCONAD RK from Kao Corporation] | | | | | | |
| Methylheptyl laurate ($C_{12}$) [NIKKOL GS-MHL] | | | | | | |
| Methylheptyl isostearate ($C_{18}$) [NIKKOL GS-MHIS] | | | | | | |
| Olive oil (main component: $C_{18}$) | | | | | | |
| Heating treatment | | | | | | |
| Set temperature (° C.) | 135-145 | 70-80 | 135-145 | 135-145 | 135-145 | 135-145 |
| Heating-up time (min) | 60 | 60 | 60 | 60 | 60 | 60 |
| Retention time (min) | 5 | 5 | 5 | 5 | 5 | 5 |

<Evaluation>

Evaluation of the oil phase compositions 1 to 17 obtained as described above were conducted as follows. Results of the evaluations are listed in Table 2.

(1) DSC Endothermic Peak Temperature and Crystal Ratio

A DSC Q2000 (trade name, manufactured by TA Instruments Japan Inc.) was used. Endothermic and exothermic temperatures for each oil phase composition were determined in one cycle of temperature-rise to temperature-fall (15° C./min) in the temperature range of from 30° C. to 200° C.

A crystallization rate of lycopene in each oil phase composition was determined by dividing the endothermic quantity of a DSC endothermic peak measured for each oil phase composition by the endothermic quantity of the DSC endothermic peak of a lycopene crystal sample having the same mass as the content of lycopene in each oil phase composition.

(2) Evaluation of Crystal by Observation by Polarizing Microscope

Visual observation of each oil phase composition just after the preparation thereof was conducted using an ECLIPSE (registered trademark) LV100POL (Nikon Corporation). The evaluation results of the visual observation were classified as follows.

Visual Evaluation

S: No crystal derived from lycopene is found.

A: Slight amount of crystal derived from lycopene is found.

B: Crystals derived from lycopene are scattered.

C: Crystals derived from lycopene are present throughout the observed image.

(3) Lycopene Residual Rate

Each oil phase composition was diluted 1062-fold with acetone to have a lycopene concentration of 0.005% by volume, and was dissolved sufficiently. Then, after filtration through a filter of 0.45 μm, the absorbance of the filtrate at the maximum peak wavelength (from 465 nm to 475 nm)

was measured with a spectrophotometer V-630 (trade name, manufactured by JASCO Corporation).

Evaluation was conducted by diluting LYCOPENE 18 (mentioned above) with acetone to have a lycopene concentration of 0.005% by volume and measuring the absorbance at the peak wavelength in the same manner as above, and a percentage in a case in which the intensity of this lycopene was taken as 100% was defined as a lycopene residual rate of each oil phase composition (lycopene residual rate (just after preparation)).

The lycopene residual ratio was further measured in the same manner as described above after storage of each oil phase composition at 40° C. for 4 months (lycopene residual rate (40° C. 4 M)).

(4) Dynamic Absorbability

The oil phase composition 1 to the oil phase composition 17 were diluted to have a lycopene concentration of 2 mg/ml, the dilution was orally administered to a non-fasted 6 week-old male rat (each group: n=4) at a dose of 10 ml/kg. After the administration, 0.4 ml of blood was collected after each of 1, 2, 3, 4, 6, 8, and 24 h.

The collected blood was centrifuged, and 0.1 ml of plasma was taken from the supernatant. The plasma was dissolved in acetone, hexane was then added, the mixture was left to stand, and the supernatant liquid was recovered. The recovered supernatant liquid was dried by solidification, and then the solid was re-dissolved in chloroform/methanol=1/1 (v/v), and a content of lycopene was measured by HPLC.

The relationship between the time from the administration to the collection of blood and the plasma lycopene concentration was illustrated graphically, and an AUC (area under the blood concentration-time curve) in a period of 8 hours after the administration with respect to each administered composition was determined as a dynamic absorption value. The results are listed in Table 2 below. A higher numerical number is evaluated as a higher concentration of active components in the blood. A symbol "-" means that no measurement was conducted (no data).

TABLE 2

|  | Example 1 Oil phase composition 1 | Example 2 Oil phase composition 2 | Example 3 Oil phase composition 3 | Example 4 Oil phase composition 4 | Example 5 Oil phase composition 5 | Example 6 Oil phase composition 6 |
|---|---|---|---|---|---|---|
| DSC endothermic peak temperature | None | None | None | None | None | None |
| Observation by polarizing microscope | S | S | S | S | A | S |
| Crystal ratio | 0% | 0% | 0% | 0% | 0% | 0% |
| Lycopene residual rate (immediately after preparation) | 100% | 99% | 100% | 100% | 100% | 99% |
| Lycopene residual rate (40° C., 4M) | 99% | 90% | 99% | 99% | 97% | 93% |
| AUC (ng * 8 h/ml) | 2870 | 2930 | — | — | 2580 | — |

|  | Example 7 Oil phase composition 7 | Example 8 Oil phase composition 8 | Example 9 Oil phase composition 9 | Example 10 Oil phase composition 10 | Example 11 Oil phase composition 11 |
|---|---|---|---|---|---|
| DSC endothermic peak temperature | None | None | None | None | None |
| Observation by polarizing microscope | S | S | S | S | S |
| Crystal ratio | 0% | 0% | 0% | 0% | 0% |
| Lycopene residual rate (immediately after preparation) | 100% | 99% | 99% | 97% | 98% |
| Lycopene residual rate (40° C., 4M) | 99% | 98% | 98% | 94% | 95% |
| AUC (ng * 8 h/ml) | — | — | — | — | — |

|  | Comparative Example 1 Oil phase composition 12 | Comparative Example 2 Oil phase composition 13 | Comparative Example 3 Oil phase composition 14 | Comparative Example 4 Oil phase composition 15 | Comparative Example 5 Oil phase composition 16 | Comparative Example 6 Oil phase composition 17 |
|---|---|---|---|---|---|---|
| DSC endothermic peak temperature | 152° C. | 152° C. | 155° C. | 145° C. | 145° C. | 140° C. |
| Observation by polarizing microscope | C | C | C | C | C | C |
| Crystal ratio | 85% | 62% | 65% | 48% | 51% | 25% |
| Lycopene residual rate (immediately after preparation) | 100% | 96% | 99% | 100% | 96% | 75% |
| Lycopene residual rate (40° C., 4M) | 84% | 84% | 97% | 78% | 84% | 53% |
| AUC (ng * 8 h/ml) | 790 | 1310 | — | 1070 | — | — |

As shown in Table 1 and Table 2, the oil phase compositions of from Example 1 to Example 11 were compositions in which no DSC endothermic peak was found and which did not substantially contain any crystal. High lycopene residual rates were indicated not only just after the preparation but also after 4-month storage at 40° C. Although crystals derived from lycopene were found to be present by observation of the oil phase composition of Example 5 by the polarizing microscope, the amount of the crystals was very slight (Evaluation A) and was less than the detection limit of DSC. Therefore, the crystal ratio calculated based on the endothermic quantity of the DSC endothermic peak is 0% in Example 5.

The results of administration experiments on rats demonstrated that all of the oil phase compositions of from Example 1 to Example 11 exhibited excellent lycopene absorbability and were carotenoid-containing compositions exhibiting high absorbability due to the suppression of lycopene crystallization.

In contrast, lycopene was not able to be stably maintained in all of Comparative Examples 1 to 3, which do not contain the defined fatty acid ester component, and Comparative Examples 4 and 5, which do not contain the defined (poly) glycerol fatty acid ester.

Example 12

An oil-in-water emulsification composition 1 which contains dispersed particles containing a carotenoid component was prepared as follows.

An aqueous phase composition shown below was heated and mixed while stirring the aqueous phase compositions in a constant-temperature bath at 70° C., and were maintained at 70° C. after confirmation of the thorough mixing.

An oil phase compositions shown below was heated and mixed for 5 minutes while stirring the oil phase compositions on a hot plate at 135° C., and the thorough mixing was confirmed.

The aqueous phase composition was added to the oil phase composition, and the resultant was stirred and mixed, and dispersed using an ultrasonic wave homogenizer. Then, the resulting coarse dispersion was further subjected to high-pressure emulsification at 200 MPa using a super-high-pressure emulsification apparatus (trade name: ALTIMIZER, manufactured by Sugino Machine Limited).

| Aqueous phase Composition | |
|---|---|
| (1) Decaglyceryl oleate[*6] | 10 parts |
| (2) Glycerol | 45 parts |
| (3) Purified water | 30 parts |
| Oil Phase Composition | |
| (1) Lycopene paste (lycopene concentration of 18%)[*7] | 2.8 parts |
| (2) Diglyceryl monostearate[*8] | 0.3 part |
| (3) Glycerol tri(caprylate/caprate)[*9] | 1.3 parts |
| (4) Mixed tocopherol[*10] | 0.6 part |

[*6]Trade name: DECAGLYN 1-O, manufactured by Nikko Chemicals Co., Ltd.,
[*7]"LYCOPENE 18" (mentioned above) from Kyowa Wellness Co., Ltd. (molecular weight of 537.0)
[*8]"NIKKOL (registered trademark) DGMS" from Nikko Chemicals Co., Ltd. (HLB = 5.0)
[*9]"COCONAD (registered trademark) MT" from Kao Corporation (HLB = 1)
[*10]Trade name: "RIKEN E OIL 800" manufactured by Riken Vitamin Co., Ltd.

Examples 13 to 16, and Comparative Examples 7 and 8

As Examples 13 to 16 and Comparative Examples 7 and 8, emulsion compositions 2 to 7 were obtained in the same manner as in Example 12 except that the kinds and contents of the oil phase compositions and the aqueous phase compositions are changed as listed in Table 3.

As each component in Table 3, the same component as that in Table 1 was used.

A numerical value indicating the blending amount of each component in Table 3 represents "part(s)".

TABLE 3

| | | Example 12 Emulsion composition 1 | Example 13 Emulsion composition 2 | Example 14 Emulsion composition 3 | Example 15 Emulsion composition 4 | Example 16 Emulsion composition 5 | Comparative Example 7 Emulsion composition 6 | Comparative Example 8 Emulsion composition 7 |
|---|---|---|---|---|---|---|---|---|
| Oil phase composition | Lycopene paste (lycopene content: 18%) | 2.8 | 2.8 | 2.8 | 2.8 | 2.8 | 2.8 | 2.8 |
| | Diglyceryl monostearate | 0.3 | | | | | | 11.6 |
| | Tetraglyceryl tristearate | | 4.80 | | | | | |
| | Tetraglyceryl pentastearate | | | 0.60 | | | | |
| | Hexaglyceryl tristearate | | | | 0.60 | | | |
| | Hexaglyceryl pentastearate | | | | | 0.60 | | |
| | Glycerol tri(caprylate/caprate) | 11.3 | 6.80 | 11.00 | 11.00 | 11.00 | 11.6 | |
| | Mixed tocopherol | 0.6 | 0.6 | 0.6 | 0.6 | 0.6 | 0.6 | 0.6 |
| Water phase composition | Decaglyceryl oleate | 10.0 | 10.0 | 10.0 | 10.0 | 10.0 | 10.0 | 10.0 |
| | Glycerol | 45.0 | 45.0 | 45.0 | 45.0 | 45.0 | 45.0 | 45.0 |
| | Water | 30.0 | 30.0 | 30.0 | 30.0 | 30.0 | 30.0 | 30.0 |

<Evaluation>
(Particle Diameter of Particle and Storage Stability)

Each of the emulsion compositions 1 to 7 obtained as described above was divided into two portions, each of the portions was filled into a 5-ml glass vial, and one vial was stored at 4° C. for 1 month. Purified water was added to each of the samples before the storage and after the 1-month storage to prepare a 1% dilution liquid, and the average particle diameter (median particle diameter) of particles in the dilution liquids based on volume standard was measured with a dynamic light scattering meter (trade name: FPAR-1000, manufactured by Otsuka Electronics Co., Ltd.). The measurement results were summarized in Table 4 below.

(Evaluation of Transparency)

Each of the 1% dilution liquids of the emulsion compositions 1 to 7 obtained as described above, before the storage and after the 1-month storage, was taken into a container having a height of 5 cm or more so that a length from the bottom of the container to a liquid level is 4 cm, and visual observation over the sample liquid was conducted from a position that is perpendicular to and above the liquid level toward the bottom of the container. Each evaluation was conducted in such a manner according to the following criteria for evaluating transparency based on whether the bottom of the container can be visually observed, and the results are listed in Table 4 below.

<Evaluation Criteria>
C: The bottom cannot be observed.
B: A bottom can be vaguely observed.
S: A bottom can be clearly observed.

TABLE 4

| | Example 12 Emulsion composition 1 | Example 13 Emulsion composition 2 | Example 14 Emulsion composition 3 | Example 15 Emulsion composition 4 | Example 16 Emulsion composition 5 | Comparative Example 7 Emulsion composition 6 | Comparative Example 8 Emulsion composition 7 |
|---|---|---|---|---|---|---|---|
| Particle diameter immediately after emulsification | 45 nm | 59 nm | 51 nm | 53 nm | 51 nm | 280 nm | 335 nm |
| Evaluation of Visual observation of transparency immediately after emulsification | S | S | S | S | S | C | C |
| Particle diameter after storage at 4° C. for 1 month | 46 nm | 58 nm | 50 nm | 54 nm | 51 nm | Unmeasurable due to precipitation | |
| Evaluation of Visual observation transparency after storage at 4° C. for 1 month | S | S | S | S | S | C | C |

As above, it is found that all of the emulsion compositions 1 to 4 containing the carotenoid-containing composition according to one embodiment of the invention have small particle diameters (60 μm or less) before the storage, and even after the 1-month storage, increase in the particle diameter is suppressed, and the particle diameters can be maintained to be small.

It is found that the very high transparency of each of the emulsion compositions 1 to 4 can be confirmed by visual observation in the case of adding the purified water to prepare the 1% dilution liquid.

Based on the results, in accordance with the invention, a carotenoid-containing composition in which crystallization is suppressed can be provided even in a case in which the composition contains a carotenoid having high crystallinity.

The disclosure of Japanese Patent Application No. 2011-253084 is incorporated herein by reference in its entirety.

All literatures, patents, patent applications, and technical standards described herein are herein incorporated by reference to the same extent as if each individual literature, patent, patent application, or technical standard was specifically and individually indicated as being incorporated by reference.

What is claimed is:

1. A carotenoid-containing composition comprising:
   a carotenoid component that is a crystalline carotenoid at least a part of which is in an amorphous state, or that is a combination of an amorphous carotenoid and a crystalline carotenoid at least a part of which is in an amorphous state;
   a (poly)glycerol fatty acid ester that comprises from one to six glycerol units, from one to six fatty acid units, and at least one hydroxyl group derived from a glycerol unit;
   a fatty acid ester component which is at least one selected from the group consisting of (i) a triester of glycerol and fatty acids and (ii) an ester of an alcohol having one hydroxyl group and a fatty acid, comprises no hydroxyl group in a molecule, and has from 10 to 60 carbon atoms in total; and
   an antioxidant;
   wherein the fatty acid ester component comprises at least one of glyceryl tricaprylate, glyceryl tricaprate, glyceryl trilaurate, glyceryl trimyristate, glyceryl tripalmitate, glyceryl tripalmitoleate, glyceryl tristearate, glyceryl trioleate, glyceryl trilinoleate, and glyceryl trilinolenate;
   a content of the fatty acid ester component is from 5 times to 200 times a total content of the carotenoid component, based on mass, and
   a total content of the (poly)glycerol fatty acid ester is from 0.01 times to 9 times a total content of the crystalline carotenoid, based on mass.

2. The carotenoid-containing composition according to claim 1, wherein a content of the crystalline carotenoid that is in an amorphous state is 50 mass % or more with respect to a total content of the carotenoid component.

3. The carotenoid-containing composition according to claim 1, wherein a content of the fatty acid ester component is from 0.8 times to 750 times a total content of the (poly)glycerol fatty acid ester, based on mass.

4. The carotenoid-containing composition according to claim 1, wherein the crystalline carotenoid is lycopene.

5. The carotenoid-containing composition according to claim 1, wherein the antioxidant comprises at least one selected from the group consisting of a compound having a phenolic hydroxyl group and an ascorbic acid compound.

6. The carotenoid-containing composition according to claim 1, wherein the antioxidant comprises at least one selected from the group consisting of aromatic carboxylic acids, cinnamic acids and ellagic acids.

7. The carotenoid-containing composition according to claim 1, wherein 90 mass % or more of the crystalline carotenoid is in an amorphous state.

8. The carotenoid-containing composition according to claim 1, wherein the carotenoid-containing composition is an oil-in-water emulsion composition comprising dispersed particles having an average particle diameter in a range of from 30 nm to 100 nm and comprising the carotenoid component.

9. A method of producing a carotenoid-containing composition comprising heating, under a temperature condition of 90° C. or more, an oil phase component-mixture liquid, the oil phase component mixture liquid comprising:

a carotenoid component that is a crystalline carotenoid at least a part of which is in an amorphous state, or that is a combination of an amorphous carotenoid and a crystalline carotenoid at least a part of which is in an amorphous state;

a (poly)glycerol fatty acid ester that comprises from one to six glycerol units, from one to six fatty acid units, and at least one hydroxyl group derived from a glycerol unit;

a fatty acid ester component that is at least one selected from the group consisting of (i) a triester of glycerol and fatty acids and (ii) an ester of an alcohol having one hydroxyl group and a fatty acid, comprises no hydroxyl group in a molecule, and has from 10 to 60 carbon atoms in total; and an antioxidant;

wherein the fatty acid ester component comprises at least one of glyceryl tricaprylate, glyceryl tricaprate, glyceryl trilaurate, glyceryl trimyristate, glyceryl tripalmitate, glyceryl tripalmitoleate, glyceryl tristearate, glyceryl trioleate, glyceryl trilinoleate, and glyceryl trilinolenate;

a content of the fatty acid ester component is from 5 times to 200 times a total content of the carotenoid component, based on mass, and a total content of the (poly)glycerol fatty acid ester is from 0.01 times to 9 times a total content of the crystalline carotenoid, based on mass.

* * * * *